(12) United States Patent
Segman

(10) Patent No.: US 10,789,725 B2
(45) Date of Patent: Sep. 29, 2020

(54) BMI, BODY AND OTHER OBJECT MEASUREMENTS FROM CAMERA VIEW DISPLAY

(71) Applicant: Yosef Segman, Zichron Yaacov (IL)

(72) Inventor: Yosef Segman, Zichron Yaacov (IL)

(73) Assignee: CNOGA MEDICAL LTD., Caesarea (IL)

( * ) Notice: Subject to any disclaimer, the term of this patent is extended or adjusted under 35 U.S.C. 154(b) by 87 days.

(21) Appl. No.: 15/959,232

(22) Filed: Apr. 22, 2018

(65) Prior Publication Data
US 2019/0325599 A1    Oct. 24, 2019

(51) Int. Cl.
   *G06T 7/60*      (2017.01)
   *G06T 7/13*      (2017.01)
   *G06T 7/149*     (2017.01)

(52) U.S. Cl.
   CPC ............... *G06T 7/60* (2013.01); *G06T 7/13* (2017.01); *G06T 7/149* (2017.01); *G06T 2207/30196* (2013.01)

(58) Field of Classification Search
   CPC .. G06T 7/60; G06T 7/13; G06T 7/149; G06T 2207/30196
   See application file for complete search history.

(56) References Cited

U.S. PATENT DOCUMENTS

| | | | | |
|---|---|---|---|---|
| 8,457,384 B2 * | 6/2013 | Smilansky | .............. | G01F 22/00 382/141 |
| 8,755,570 B2 * | 6/2014 | Gomas | ................. | G06K 9/6209 382/110 |
| 8,885,916 B1 * | 11/2014 | Maurer | ............... | G06K 9/6202 382/141 |

(Continued)

FOREIGN PATENT DOCUMENTS

| | | |
|---|---|---|
| CN | 106666903 A | 5/2017 |
| GB | 2518931 A | 4/2015 |
| WO | 2013055223 A1 | 4/2013 |

OTHER PUBLICATIONS

Habib Bipembi et al: "Calculation of Body Mass Index using Image Processing Techniques PhD thesis view project parity Progression estimation and categorical Analysis of Birth cohort data in ghana View project Calculation of Body Mass Index using Image Processing Techniques", International Journal of Artificial Intelligence and Mechatronics vol. ISSN, Jul. 31, 2015.

*Primary Examiner* — Brenda C Bernardi
(74) *Attorney, Agent, or Firm* — Mark M. Friedman

(57) ABSTRACT

Apparatus for determining height, width, weight or body mass index (BMI) of a subject or distance along an object. For BMI, the apparatus includes a digital camera; an application; a processing unit for storing the vertical and horizontal dimensions of known substantially rectangular reference objects. A user interface prompts and receives the type of reference object held by the user or its dimensions. For each of the vertical and horizontal dimensions, a magnitude in pixels and in distance of the reference object to form a ratio and a pixel magnitude of the vertical and horizontal dimensions of the subject in the image(s), is used to derive an estimated height and width of the subject from the pixel magnitude of the vertical and horizontal dimensions of the subject in the image(s). In some embodiments, the number of pixels occupied by the subject in the image(s) is used with a look-up table.

11 Claims, 25 Drawing Sheets

(56) References Cited

U.S. PATENT DOCUMENTS

| | | | | |
|---|---|---|---|---|
| 8,923,650 B2* | 12/2014 | Wexler | | G01C 11/04 |
| | | | | 382/286 |
| 9,020,259 B2* | 4/2015 | Bhagavathy | | G06K 9/00711 |
| | | | | 382/165 |
| 9,109,891 B2* | 8/2015 | Yamato | | G01C 11/06 |
| 9,142,028 B2* | 9/2015 | Banhazi | | G06T 7/60 |
| 9,245,337 B2* | 1/2016 | Schmidt | | G06K 9/6253 |
| 9,304,332 B2* | 4/2016 | Fonte | | B29D 12/02 |
| 9,305,218 B2* | 4/2016 | Lewis | | G06K 9/00771 |
| 9,311,556 B2* | 4/2016 | Banhazi | | A01K 29/00 |
| 9,489,743 B2* | 11/2016 | Spector | | G06T 7/60 |
| 2004/0153309 A1* | 8/2004 | Lin | | G06F 17/27 |
| | | | | 704/9 |
| 2004/0175034 A1* | 9/2004 | Wiemker | | G06T 7/12 |
| | | | | 382/173 |
| 2005/0077469 A1* | 4/2005 | Kaushal | | B60R 21/01516 |
| | | | | 250/330 |
| 2007/0122017 A1* | 5/2007 | Binnig | | G06K 9/00127 |
| | | | | 382/128 |
| 2013/0064432 A1* | 3/2013 | Banhazi | | G06T 7/60 |
| | | | | 382/110 |
| 2013/0179288 A1 | 7/2013 | Moses et al. | | |
| 2013/0265396 A1* | 10/2013 | Surma | | G03B 13/18 |
| | | | | 348/47 |
| 2013/0274906 A1* | 10/2013 | Shafter | | G06Q 10/10 |
| | | | | 700/92 |
| 2014/0270395 A1* | 9/2014 | Jones | | G06T 7/62 |
| | | | | 382/110 |
| 2016/0217591 A1* | 7/2016 | Krupnik | | G06T 7/60 |
| 2019/0050427 A1* | 2/2019 | Wiesel | | G06K 9/3241 |
| 2019/0244407 A1* | 8/2019 | Wiesel | | G06K 9/00369 |

* cited by examiner

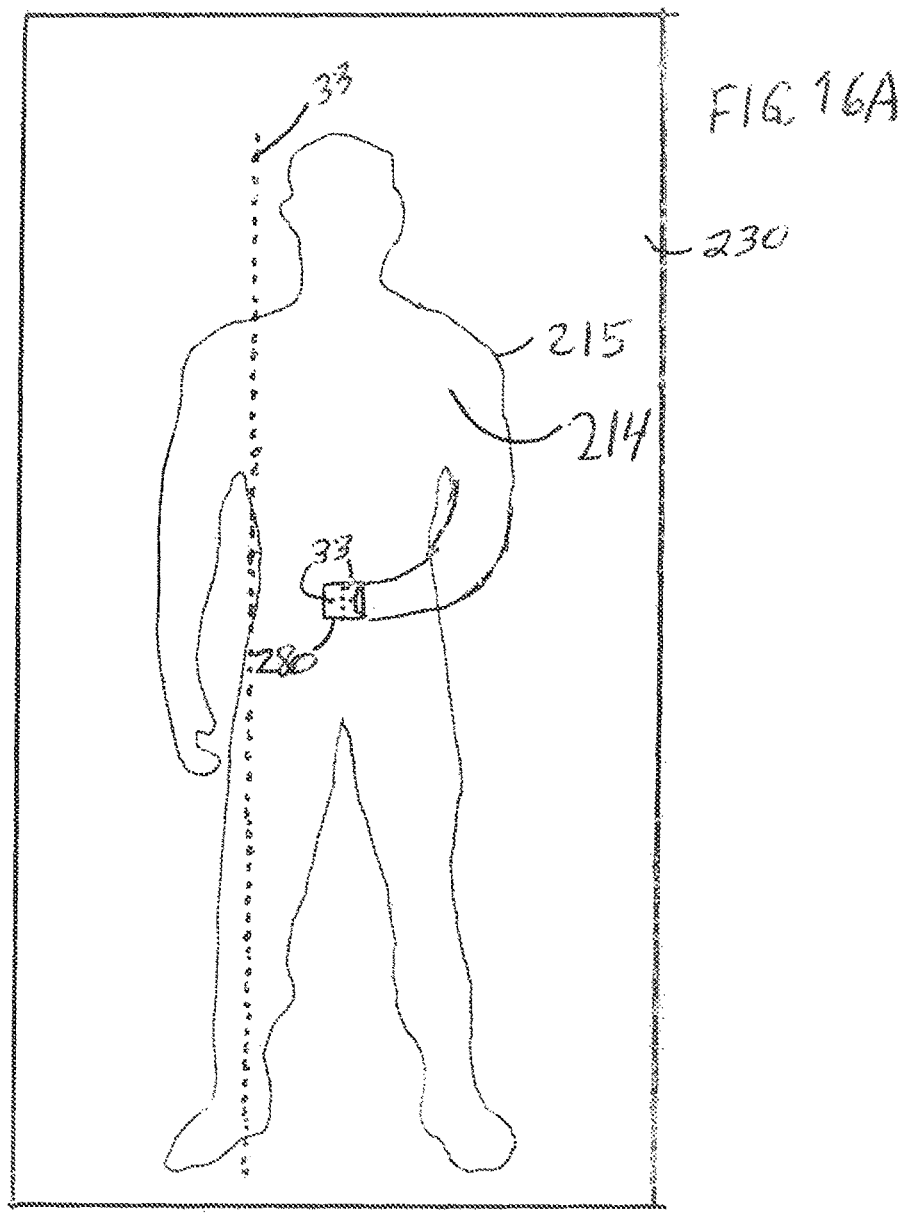

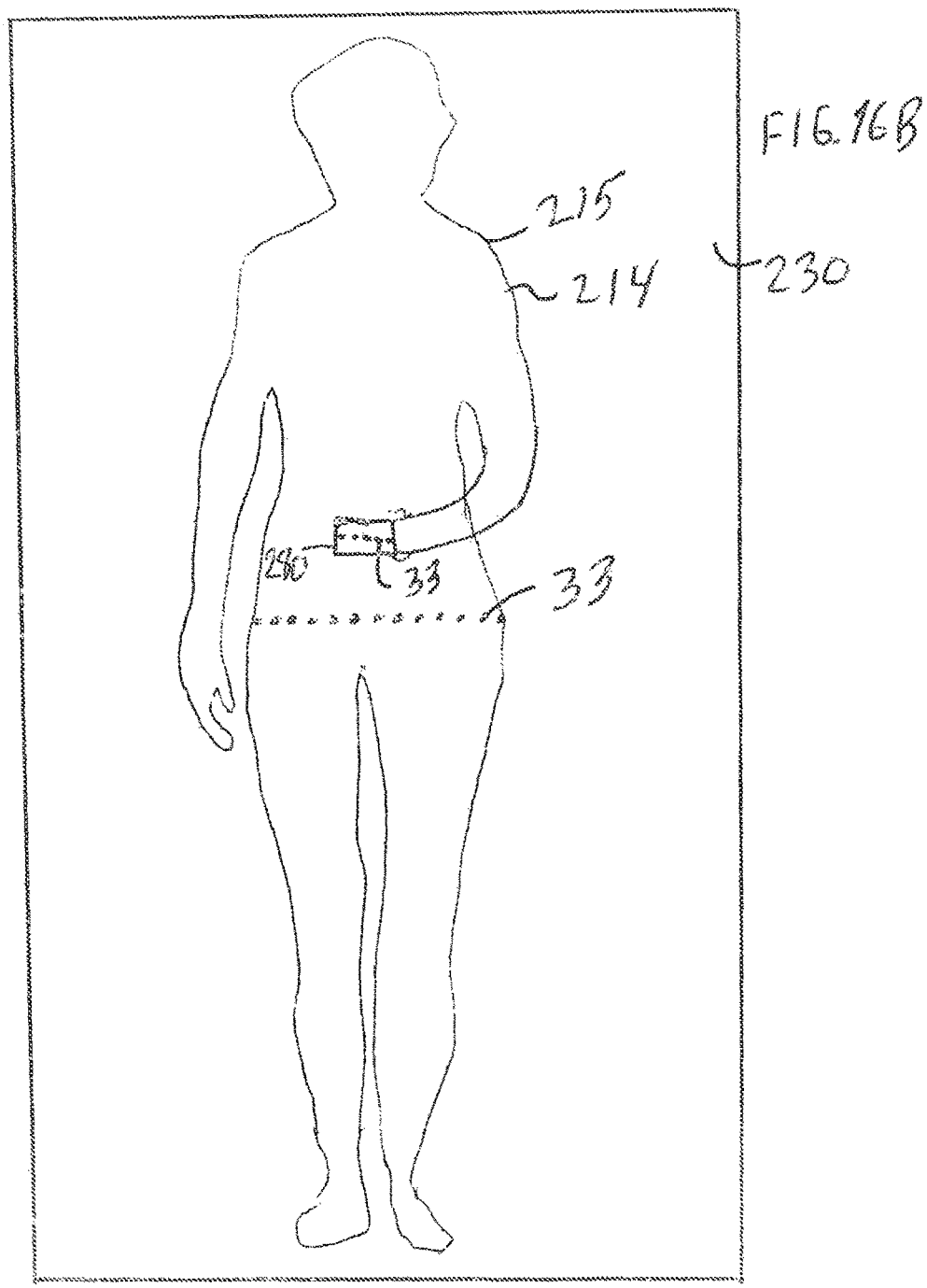

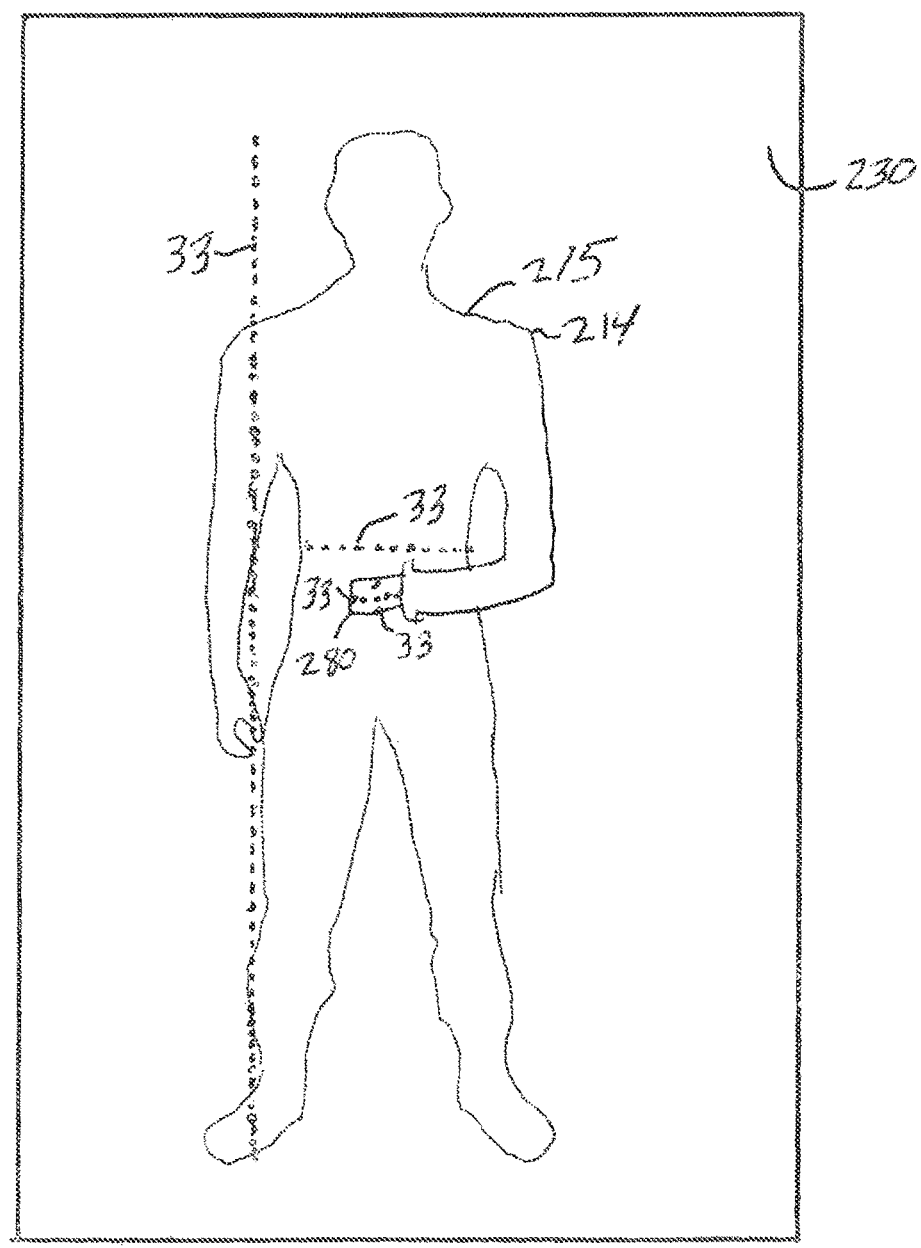

BMI, BODY AND OTHER OBJECT MEASUREMENTS FROM CAMERA VIEW DISPLAY

FIELD AND BACKGROUND OF THE INVENTION

The invention relates to apparatuses and methods for determining a height, width, weight and/or body mass index (BMI) or a subject or for determining object measurements and/or an estimate thereof, and in particular a camera that provides such an apparatus and/or method.

Body mass index, known as BMI, is used as an indicator for obesity, blood pressure, hypertension and wellness. It is known to calculate BMI by having a subject stand on a scale to determine the subject's weight and by using a ruler to measure the subject's height.

It is desirable to determine a subject's height, width, weight and/or BMI conveniently, simply and/or speedily.

SUMMARY OF THE INVENTION

One aspect of the invention is an apparatus configured to approximate a height of a subject, comprising a digital camera having a view display for displaying the subject entirely within the view display, an application; a processing unit for executing the application, the application including program code, and a memory for storing an image of a subject viewed in the view display and for storing at least the vertical dimension of known substantially rectangular reference objects, the application having a user interface configured to prompt and receive at least one of the following two user inputs: (i) the type of the known substantially rectangular reference object held by the user or (ii) at least the vertical dimension of a substantially rectangular reference object held by the user, the processing unit configured to determine (i) a magnitude, as measured in pixels in the image, of the vertical dimension of the reference object held by the user, (ii) a magnitude of the actual vertical dimension of the reference object held by the user known from one of the two user inputs, (iii) a magnitude, as measured in pixels in the image, of the vertical dimension of the subject in the image, (iv) a ratio of the magnitude, as measured in pixels in the image, of the vertical dimension of the reference object, and the magnitude of the actual vertical dimension of the reference object, and (v) an estimated height of the subject from the magnitude, as measured in pixels in the image, of the vertical dimension of the subject in the image, and from the ratio.

In some embodiments, the apparatus further comprises at least one of a credit card or a patch.

A further aspect of the invention is an apparatus configured to approximate a body size parameter of a subject, comprising a digital camera having a view display for displaying the subject entirely within the view display; an application; a processing unit for executing the application, the application including program code, and a memory for storing at least one image of a subject viewed in the view display and for storing at least the horizontal dimension of known substantially rectangular reference objects, the application having a user interface configured to prompt and receive at least one of the following two user inputs: (i) the type of the known substantially rectangular reference object held by the user or (ii) at least the horizontal dimension of a substantially rectangular reference object held by the user, the processing unit configured to determine (a) a magnitude, as measured in pixels in the at least one image, of the horizontal dimension of the reference object held by the user, (b) a magnitude of the actual horizontal dimension of the reference object held by the user known from one of the two user inputs, (c) a magnitude, as measured in pixels in the at least one image, of the horizontal dimension of the subject in the at least one image, (d) a ratio of the magnitude, as measured in pixels in the at least one image, of the horizontal dimension of the reference object, and the magnitude of the actual horizontal dimension of the reference object, (e) an estimated width of the subject in at least one location of the subject from the magnitude, as measured in pixels in the at least one image, of the horizontal dimension of the subject in the at least one image, and from the ratio.

In some embodiments, the apparatus further comprises at least one of a credit card and a patch.

In some embodiments, the processing unit is configured for storing a vertical dimension of the known substantially rectangular reference objects and the user interface is configured to prompt and receive at least one of the following two user inputs: (i) the type of the known substantially rectangular reference object held by the user or (ii) the vertical dimension and the horizontal dimension of the substantially rectangular reference object held by the user, the processing unit is also configured to determine (i) a magnitude, as measured in pixels in the at least one image, of the vertical dimension of the reference object held by the user, (ii) a magnitude of the actual vertical dimension of the reference object held by the user known from one of the two user inputs, (iii) a magnitude, as measured in pixels in the image, of the vertical dimension of the subject in the at least one image, (iv) a ratio of the magnitude, as measured in pixels in the image, of the vertical dimension of the reference object, and the magnitude of the actual vertical dimension of the reference object, and (v) an estimated height of the subject from the magnitude, as measured in pixels in the at least one image, of the vertical dimension of the subject in the at least one image, and from the ratio, and wherein the processing unit is configured to determine an estimated weight of the subject from the estimated height in the at least one image and from the estimated width of the subject in the at least one location in the at least one image.

In some embodiments, the estimated weight is determined from the estimated height and estimated width in the at least one location in the at least one image based on a look-up table cross-referencing weights with combinations of heights and widths.

In some embodiments, the at least one location of the subject is in a front belly area of the subject. In some embodiments, the at least one location of the subject is a profile belly area of the subject.

In some embodiments, the at least one location of the subject is a front belly area of the subject in a first image of the at least one image and a profile belly area of the subject in a second image of the at least one image. In some embodiments, the processing unit is configured to determine an estimated weight of the subject from the estimated height and from the estimated widths of the subject in the first and second images of the at least one image.

Another aspect of the invention is an apparatus configured to determine an estimated body size parameter of a subject, comprising a digital camera having a view display for displaying the subject entirely within the view display; an application; a processing unit for executing the application, the application including program code, and a memory for storing at least one image of the subject viewed in the view display, the processing unit configured to determine a number of pixels occupied by the subject in the at least one image and to determine the estimated body size parameter of the subject from at least one look-up table correlating the number of pixels occupied by the subject with the estimated body size parameter.

In some embodiments, the at least one image comprises a front image and a profile image, wherein the at least one look-up table comprises a first look-up table correlating the number of pixels occupied in the front image with the estimated body size parameter and a second look-up table correlating the number of pixels occupied in the profile image with the estimated body size parameter and wherein the estimated body size parameter is determined by the processing unit using at least one of (i) the front image and first look-up table and (ii) profile image and second look-up table.

In some embodiments, the estimated body size parameter is an estimated weight of the subject.

In some embodiments, the estimated body size parameter is an estimated volume of the subject.

In some embodiments, the body size parameter is an estimated area of the subject, along the two dimensions most completely visible when viewing the subject from an image of the at least one image.

A still further aspect of the invention is an apparatus for determining a body mass index (BMI) of a subject, comprising a digital camera having a view display for displaying the subject entirely within the view display; an application; a processing unit for executing the application, the application including program code, and a memory for storing at least one image of a subject viewed in the view display and for storing the vertical and horizontal dimensions of known substantially rectangular reference objects, the application having a user interface configured to prompt and receive at least one of the following two user inputs: (i) the type of the known substantially rectangular reference object held by the user or (ii) the vertical and horizontal dimensions of a substantially rectangular reference object held by the user, the processing unit configured to determine (A) a magnitude, as measured in pixels in the at least one image, of the vertical dimension of the reference object held by the user, a magnitude of the actual vertical dimension of the reference object held by the user known from one of the two user inputs, a magnitude, as measured in pixels in the at least one image, of the vertical dimension of the subject in the at least one image, a vertical ratio of the magnitude, as measured in pixels in the at least one image, of the vertical dimension of the reference object, and the magnitude of the actual vertical dimension of the reference object, an estimated height of the subject from the magnitude, as measured in pixels in the at least one image, of the vertical dimension of the subject in the at least one image, and from the vertical ratio; (B) (I) an estimated weight of the subject from a number of pixels occupied by the subject in the at least one image together with a look-up table correlating the number of pixels occupied by the subject with the estimated weight of the subject; or (II) (a) a magnitude, as measured in pixels in the at least one image, of the horizontal dimension of the reference object held by the user, (b) a magnitude of the actual horizontal dimension of the reference object held by the user known from one of the two user inputs, (c) a magnitude, as measured in pixels in the at least one image, of the horizontal dimension of the subject in the at least one image, (d) a horizontal ratio of the magnitude, as measured in pixels in the at least one image, of the horizontal dimension of the reference object, and the magnitude of the actual horizontal dimension of the reference object, (e) an estimated width of the subject in at least one location of the subject from the magnitude, as measured in pixels in the at least one image, of the horizontal dimension of the subject in the at least one image, and from the horizontal ratio, (f) the estimated weight of the subject from the estimated width, the estimated height and from a look-up table correlating estimated weights with combinations of estimated widths and heights, the processing unit configured to determine the BMI from the determined estimated height and estimated weight.

In some embodiments, the processing unit is configured to determine the estimated weight of the subject from the number of pixels occupied by the subject in the at least one image together with the look-up table correlating the number of pixels occupied by the subject with the estimated weight of the subject.

In some embodiments, the apparatus further comprises the substantially rectangular reference object, wherein the reference object is one of a credit card and a patch.

Another aspect of the invention is an apparatus configured to approximate a distance from point A on a subject or object to point B on the subject or object, comprising a digital camera having a view display for displaying a subject or object within the view display; an application having an interface to the camera; a processing unit for executing the application, the application including program code, and a memory for storing an image of a subject or object viewed in the view display and for storing vertical and horizontal dimensions of known substantially rectangular reference objects, the processing unit configured to determine an estimated distance, along a straight line or along a curve, from point A on the subject or object to Point B on the subject or object, by using the application; the application having a user interface configured to prompt and receive at least one of the following two user inputs: (i) the type of the known substantially rectangular reference object held by the user and (ii) the vertical and horizontal dimension of a substantially rectangular reference object held by the user, the processing unit configured to determine the estimated distance from the point A to the Point B on the subject or object from (i) a magnitude, as measured in pixels in the image, of the vertical or horizontal dimension of the reference object held by the user, (ii) a magnitude of the actual vertical or horizontal dimension of the reference object held by the user known from one of the two user inputs, (iii) a magnitude, as measured in pixels in the image, from point A to Point B on the subject or object in the image, and a ratio of "(i)" and "(ii)".

In some embodiments, the object is an article of clothing.

A yet still further aspect of the invention is an apparatus configured to approximate a body mass index (BMI) of a subject using an optical mechanism, comprising a digital camera having a view display for displaying the subject entirely in the view display; an application having an interface to the camera, the view display including a top border known or calculated by the application and a side border known or calculated by the application, the application integrated with a filter configured to determine a contour of a subject in an image memory, the contour including a topmost point or bottommost point and including left and right side points at a mid-torso area of the subject, the subject visible entirely within the view display, the camera having a known optical magnification factor, a distance mechanism comprising either a user input prompt for the user to input the distance factor or a distance factor prompt informing the user how far to place the subject from the camera, the distance mechanism for obtaining the distance factor between the camera and the subject to be imaged at a time at least one image of the subject is created; a processing unit for executing the application, the application including program code, and a memory for storing the at least one image, the known optical magnification factor and the known distance factor at the time the at least one image of the subject is created, the processing unit configured to determine (A) an estimated height of the subject derived from (i) the known distance factor, (ii) the known optical magnification factor and (iii) a distance, as measured in pixels, from the topmost point of the subject to the top border or from the topmost point of the subject to the bottommost point of the subject, and (B) an estimated weight of the subject derived from the estimated height and from at least one of the following (i) the number of pixels occupied by the subject together with a look-up table converting the number of pixels occupied with the estimated weight, (ii) a width of the contour of the subject obtained from the left and right side points and from a number of pixels from the left side point to a left side border and a number of pixels from the right side point to a right side border, or the width of the contour of the subject obtained from a number of pixels in a maximum continuous horizontal width of the contour, whether the subject poses in a front view or a side view, the processing unit configured to determine the BMI from the determined estimated height and estimated weight.

In some embodiments, the application is configured to calculate the number of pixels occupied by the subject and wherein the processing unit is configured to determine the estimate weight from the number of pixels occupied by the subject together with the look-up table.

In some embodiments, the application is configured to calculate a number of pixels from the left or right side point to the side border and wherein the processing unit is configured to determine the estimated weight from the width of the contour of the subject. In some embodiments, the processing unit is configured to determine the width of the contour of the subject from the left and right side points and from the number of pixels from the left and right side points to the side border. In some embodiments, the application is configured to calculate the number of pixels in the maximum continuous horizontal width of the contour and wherein the processing unit is configured to determine the estimated weight of the subject from the estimated height and the width of the contour of the subject and to determine the width of the contour of the subject from the number of pixels in the maximum continuous horizontal width of the contour. In some embodiments, the contour comprises a sequence of points at outer portions of the subject. In some embodiments, the estimated weight is derived from the estimated height and the width of the contour using a look-up table cross-referencing weights and combinations of heights and widths.

These and other features, aspects and advantages of the invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 16A is a schematic illustration of a subject shown in a digital camera view display holding a reference object;

FIG. 16B is a schematic illustration of a subject shown in a digital camera view display holding a reference object;

FIG. 16C is a schematic illustration of a subject shown in a digital camera view display holding a reference object;

DETAILED DESCRIPTION OF THE INVENTION

Figure 1:
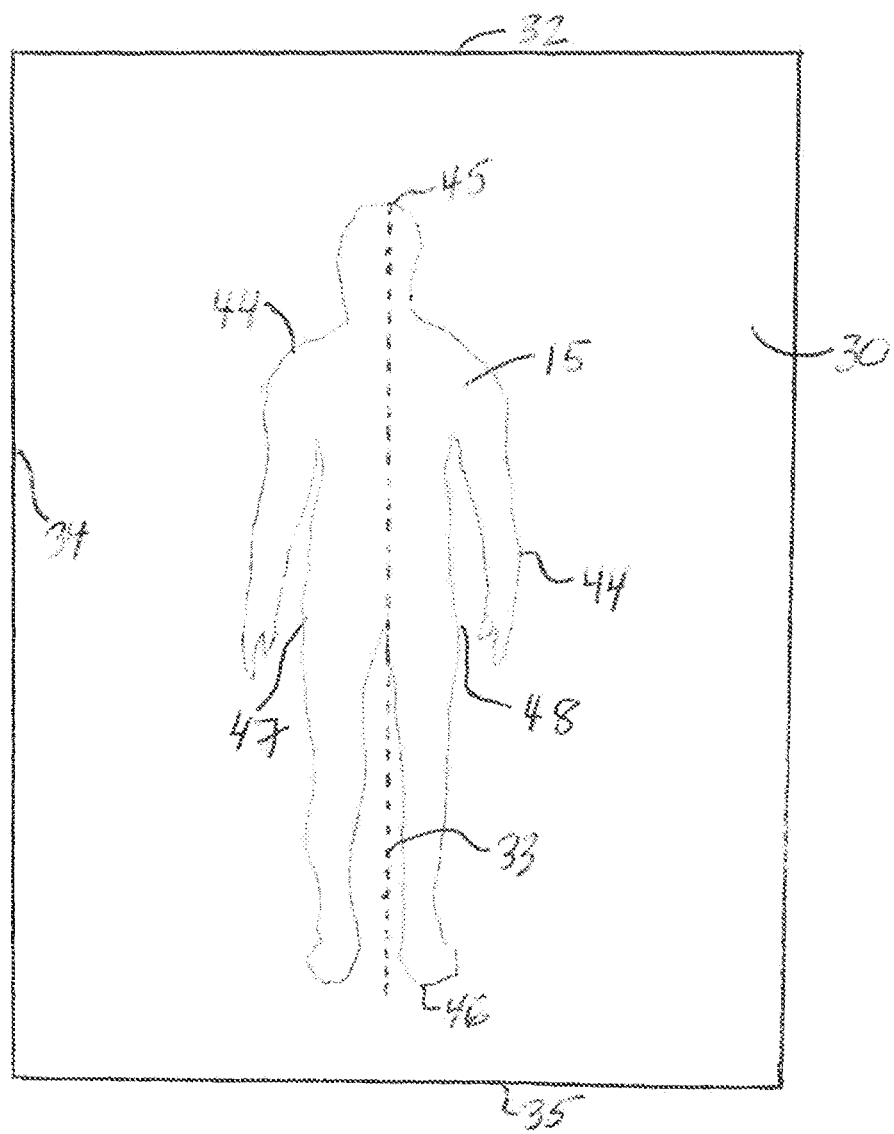
FIG. 1 is a schematic illustration of a subject shown in a digital camera view display, in accordance with one embodiment of the invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

This invention generally provides a new apparatus and/or method to, among other things, estimate distance on a body. In one example, this is used to estimate the height of the body, the width of the body or the distance from point A to point B on the body where points A and B are on the body. In one embodiment, it is used to estimate the height of a subject, the width of the subject (from the front and/or profile) in at least one location of the body and/or to estimate the body weight of another body size parameter (i.e. volume or area) from the height of the body and from at least one width location of the body, or in other embodiments from the front and profile of the belly area or other suitable areas of the body. In some embodiments, the height of the body and the weight of the body of the subject are used to estimate an individual's BMI. In general, in this patent application, when look-up tables are used to correlate weights or other body size parameters of a subject with heights, widths or other measured dimensions of the subject 214, the look-up tables may be for an entire population of subjects or may be in other embodiments for a particular subdivision of the subject, for example gender and/or age and/or other categories.

In one embodiment, the invention generally provides an estimate of one's body-mass index (BMI) from a digital camera's view display without the need to touch the subject, i.e. from a distance. The BMI is estimated by the digital camera. The digital camera may be a stand-alone appliance or it may be part of a smart phone, cell phone. The BMI may also be estimated using an image sensor. This avoids the inconvenience of having to weigh the subject (214, 14) or to directly measure a height of the subject (214, 14) with a ruler or to go to a medical professional to obtain the BMI. For example, the equipment that is needed to compute weight (i.e. a scale) and/or height might not be available at the time the user wants to estimate his or her BMI. Furthermore, in certain embodiments in which the apparatus forms part of a smartphone or cell phone, this renders it unnecessary to purchase a further appliance.

In another embodiment, points A and B are points on an object such as an article of clothing, for example such an article held by someone in a clothing store. In that case, the invention allows the prospective purchaser to measure the size of a part of the clothing and/or to measure a part of their own body to see if the clothing would fit, for example without trying on the clothing.

The principles and operation of a BMI, Body and Other Object Measurements From Camera View Display may be better understood with reference to the drawings and the accompanying description.

Figure 17:
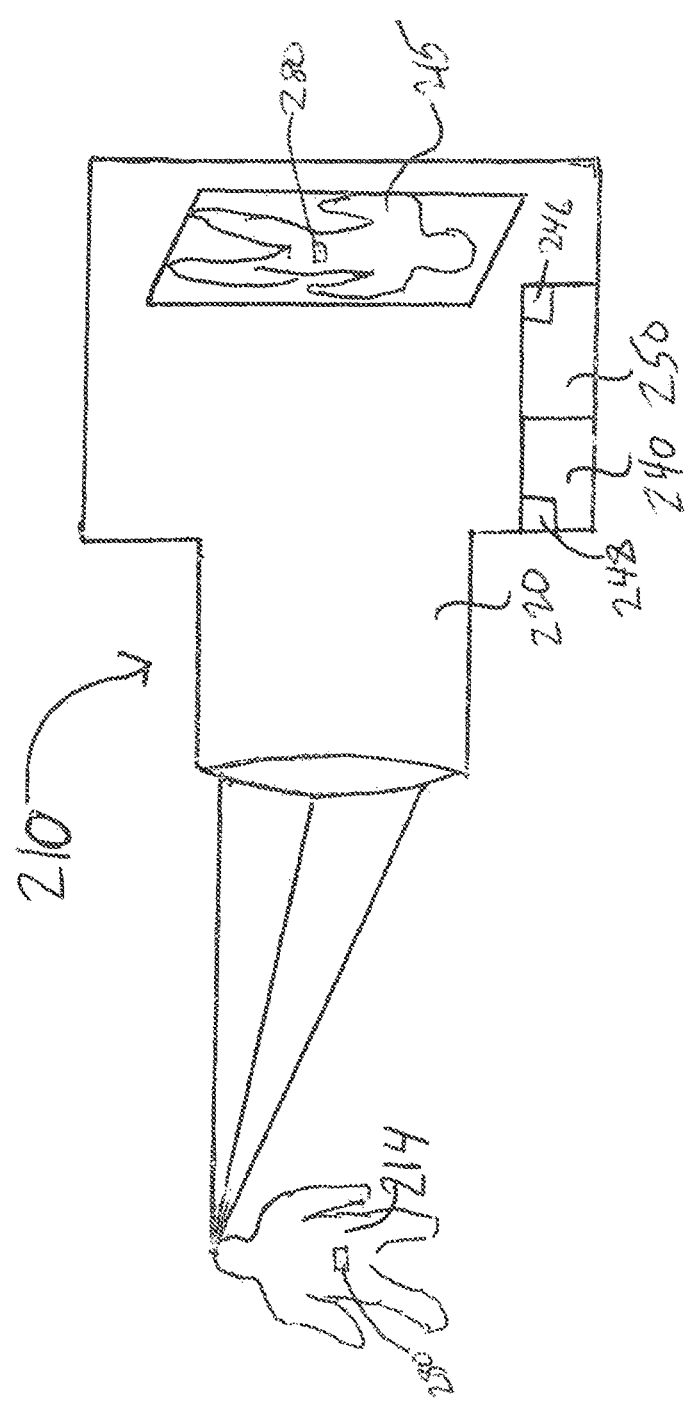
FIG. 17 is a schematic illustration of the operation of a digital camera, in accordance with one embodiment of the invention.

As shown in FIG. 16A and FIG. 17, an apparatus 210 is configured in some embodiments to approximate a height of a subject 214, using an optical mechanism. Apparatus 210 comprises a digital camera 220 having a view display 230 for displaying the subject 214, for example for viewing the subject 214 entirely within the view display.

Apparatus 210 may also comprise an application 240 and a processing unit 250 for executing the application 240, the application including program code 248, and a memory 246 for storing an image 215 or multiple images 215 or at least one image 215 of a subject 214 viewed in the view display 230 and for storing at least the vertical dimension of known substantially rectangular reference objects. Application 240 may either be downloadable in any suitable manner for example from the Internet or an external device or alternatively may be already built into the camera, or may be available through other ways.

Credit cards are an example of substantially rectangular reference objects 280 whose vertical and horizontal dimensions are known. Credit cards come in standard sizes. Even credit cards from different banks or companies (Visa®, Mastercard®, etc.) have the same horizontal and vertical dimensions, namely approximately 3 and ⅜ inches by approximately 2 and ⅛ inches, or approximately 8.5 cms by approximately 5.4 cms. Moreover, almost everyone carries at least one credit card with them almost all of the time. Certain patches used for medical purposes (for examples bandaging) are also examples of substantially rectangular reference objects whose vertical and horizontal dimensions are known and standardized.

Application 240 may have a user interface configured to prompt and receive at least one of the following two user inputs: (i) the type of the known substantially rectangular reference object held by the user or (ii) at least the vertical dimension of a substantially rectangular reference object held by the user.

In this patent application, "At least one of A or B" means A or B or both A and B. "At least one of A and B" also means A or B or both A and B.

For example, the user interface may prompt the user to state whether the user has a credit card that the user plans to use as a reference object in the at least one image 215 of the subject, for example by holding the credit card on his chest such that the vertical dimension of the card is substantially parallel to the height of the subject, as shown in FIG. 16A. The vertical dimension can be the card's short or long side, depending on how the card is held.

If the user inputs "Yes" or the equivalent, then the processing unit 250 knows it needs to simply access the previously stored and therefore known vertical and horizontal dimensions of a standard credit card as the magnitude of the actual vertical and horizontal dimensions of the reference object held by the user.

If the user inputs "No" or the equivalent, in some embodiments, the user interface of application 240 may prompt the user to state whether the user has a patch or other object that the user plans to use as a substantially rectangular reference object in the image of the subject. In certain embodiments, the prompt about the credit card and the prompt about the patch or other cards can be unified into a single prompt.

If the user inputs "Yes" or the equivalent, to a further prompt about the patch or other reference object, then the processing unit 250 knows it needs to simply access the previously stored and therefore known vertical and horizontal dimensions of that object, such as a patch, as the magnitude of the vertical and horizontal dimensions of the reference object held by the user.

Depending on the embodiment, after one or a certain number of prompts, if the user inputs "No" or the equivalent, in relation to objects whose vertical and horizontal dimensions are known, then in some embodiments the user interface of application 240 may prompt the user to state whether the user would like to input dimensions of a substantially rectangular reference object that the user plans to hold in the at least one image 215 (for example by holding the object on the user's chest such that one of the two dimensions (horizontal or vertical) of the card is substantially parallel to the ground that the subject is standing on, as shown in FIG. 1 or is substantially perpendicular to the height of the subject).

If the user inputs "Yes" or the equivalent, the user may then be prompted to actually input the vertical dimension. In some embodiments, these two prompts may be combined, for example by prompting the user as follows or something that is equivalent of what follows: "Do you have the vertical dimension of another reference object. If so, please enter."

All of the above prompts are merely non-limiting examples of the user interface prompts configured to obtain either an input of the type of substantially rectangular reference object that the user will hold in the at least one image 215 of the subject (and whose dimensions the processing unit 250 already has stored) or the actual dimensions of a particular substantially rectangular reference object that the user will hold in the at least one image 215 of the subject.

In one embodiment, processing unit 250 is configured to determine the subject's estimated height by determining:

(i) a magnitude, as measured in pixels 33 in the at least one image 215, of the vertical dimension of the reference object 280 held by the user, (ii) a magnitude of the actual vertical dimension of the reference object 280 held by the user known from one of the two user inputs, (iii) a magnitude, as measured in pixels 33 in the image, of the vertical dimension of the subject in the at least one image 215, (iv) a ratio of the magnitude, as measured in pixels in the at least one image, of the vertical dimension of the reference object 280, and the magnitude of the actual vertical dimension of the reference object 280, and (v) an estimated height of the subject from the magnitude, as measured in pixels 33 in the image, of the vertical dimension of the subject in the at least one image 215, and from the ratio.

In another embodiment shown in FIG. 16B, an apparatus 210 is configured to approximate a body size parameter of a subject, such as a width (or weight, volume or area) of the subject in at least one location of the subject. In this embodiment, apparatus 210 comprises a digital camera 220 having a view display 230 for displaying the subject entirely within the view display; an application 240 and a processing unit 250 for executing the application 240, the application including program code, and a memory for storing at least one image of the subject (or another object) in the view display 230 and for storing at least the horizontal dimension of known substantially rectangular reference objects 280.

Application 240 may have a user interface configured to prompt and receive at least one of the following two user inputs: (i) the type of the known substantially rectangular reference object 280 held by the user or (ii) at least the horizontal dimension of a substantially rectangular reference object 280 held by the user.

For example, the user interface may prompt the user to state whether the user has a credit card that the user plans to use as a reference object in the at least one image of the subject, for example by holding the credit card on his chest such that the horizontal dimension of the card is substantially perpendicular to the height of the subject, as shown in FIG. 16B. The horizontal dimension can be the card's short or long side, depending on how the card is held.

The discussion and options relating to the user interface in this embodiment is the same as the discussion relating to the user interface in the embodiment for measuring the height except that the relevant dimension here is the horizontal dimension.

If the user inputs "Yes" or the equivalent, then the processing unit 250 knows it needs to simply access the previously stored and therefore known horizontal dimensions of a standard credit card as the magnitude of the actual horizontal dimensions of the reference object held by the user.

If the user inputs "No" or the equivalent, in some embodiments, the user interface of application 240 may prompt the user to state whether the user has a patch or other object that the user plans to use as a substantially rectangular reference object in the at least one image of the subject. In certain embodiments, the prompt about the credit card and the prompt about the patch or other cards can be unified into a single prompt.

If the user inputs "Yes" or the equivalent, to a further prompt about the patch or other reference object, then the processing unit 250 knows it needs to simply access the previously stored and therefore known horizontal dimensions of that object 280, such as a patch, as the magnitude of the horizontal dimension of the reference object 280 held by the user.

Depending on the embodiment, after one or a certain number of prompts, if the user inputs "No" or the equivalent, in relation to objects whose horizontal dimensions are known, then in some embodiments the user interface of application 240 may prompt the user to state whether the user would like to input dimensions of a substantially rectangular reference object that the user plans to hold in the at least one image 215 (for example by holding the object on the user's chest such that the horizontal dimension of the card is substantially perpendicular to a height of the subject, as shown in FIG. 16B.

If the user inputs "Yes" or the equivalent, the user may then be prompted to actually input the horizontal dimension. In some embodiments, these two prompts may be combined, for example by prompting the user as follows or something that is equivalent of what follows: "Do you have the horizontal dimension of another reference object. If so, please enter."

All of the above prompts are merely non-limiting examples of the user interface prompts configured to obtain either an input of the type of substantially rectangular reference object that the user will hold in the at least one image of the subject (and whose dimensions the processing unit 250 already has stored) or the actual dimensions of a particular substantially rectangular reference object that the user will hold in the at least one image 215 of the subject.

In one embodiment, processing unit 250 is configured to determine the subject's estimated width by determining:

(a) a magnitude, as measured in pixels 33 in the at least one image, of the horizontal dimension of the reference object 280 held by the user, (b) a magnitude of the actual horizontal dimension of the reference object 280 held by the user known from one of the two user inputs, (c) a magnitude, as measured in pixels 33 in the at least one image, of the horizontal dimension of the subject 214 in the at least one image, (d) a ratio of the magnitude, as measured in pixels 33 in the at least one image 215, of the horizontal dimension of the reference object 280, and the magnitude of the actual horizontal dimension of the reference object 280, (e) an estimated width of the subject 214 in at least one location of the subject from the magnitude, as measured in pixels 33 in the at least one image, of the horizontal dimension of the subject 214 in the at least one image 215, and from the ratio.

In a further embodiment, processing unit 250 is configured to determine an estimated weight of subject 214 from the estimated width of the subject 214 already determined. For example, the estimated weight is determined from the estimated width based on a look-up table, for example a look-up table stored in a memory of processing unit 250 (or stored externally in other embodiments) as well as from the estimated height of the subject. In this patent application, the term "look-up table" is not limited to a table but includes any computerized cross-reference mechanism correlating one or a combination of variables to another variable (for example a width and height of a subject with a weight or estimated weight of the subject, or in another example a number of pixels 33 occupied by a subject in at least one image with a weight or an estimated weight of the subject).

The at least one location may be a belly, a waist, a hips, a belly area, etc. In one embodiment, the at least one location of the subject is in a mid-torso area of the subject and the processing unit is configured to determine an estimated weight of the subject from the estimated width of the subject, using a look-up table.

In another embodiment, the at least one location of the subject is in a belly area of the subject and the processing unit is configured to determine an estimated weight of the subject from the estimated width of the subject using a look-up table.

In some embodiments, the waist area of the subject is used as the estimated width so to correlate with the weight of the subject in a look-up table. In some embodiments, the width at the area of the hips of the subject is used in a look-up table as a correlation for determining the estimated weight of the subject. In some embodiments, the average width of the subject in the area between the waist of the subject to the hips of the subject, is used as a correlation for determining the estimated weight of the subject. The term "mid-torso area", which is used in certain embodiments to describe the area on the subject that is used as a correlation for determining the subject's estimated weight, encompasses points along the waist area, the hip area, the area between the waist area and the hip area, and areas adjacent to the hip and waist that may be a widest point of the subject (not including the chest area or shoulders of the subject).

In a different embodiment, the chest or shoulders are used to correlate with the weight of the subject.

The reference object may be a credit card, a patch or another reference object that is substantially rectangular. If it is not of known dimensions, the user will have to input the actual horizontal dimension.

Since in this embodiment the estimated weight is also determined from the subject's estimated height, the processing unit 250 is also configured to store and process the details mentioned above in the embodiment for determining the estimated height. For example, the processing unit 250 is configured for storing a vertical dimension of the known substantially rectangular reference objects 280 and the user interface is configured to prompt and receive at least one of the following two user inputs: (i) the type of the known substantially rectangular reference object held by the user or (ii) the vertical dimension and the horizontal dimension of the substantially rectangular reference object held by the user (not just the horizontal dimension).

Furthermore, processing unit 250 is also configured to determine (i) a magnitude, as measured in pixels in the at least one image 215, of the vertical dimension of the reference object held by the user, (ii) a magnitude of the actual vertical dimension of the reference object held by the user known from one of the two user inputs, (iii) a magnitude, as measured in pixels in the at least one image 215, of the vertical dimension of the subject in the at least one image 215, (iv) a ratio of the magnitude, as measured in pixels in the at least one image 215, of the vertical dimension of the reference object, and the magnitude of the actual vertical dimension of the reference object, and (v) an estimated height of the subject from the magnitude, as measured in pixels in the at least one image 215, of the vertical dimension of the subject in the at least one image, and from the ratio. Accordingly, in this embodiment, processing unit 250 is configured to determine an estimated weight of the subject from the estimated height in the image and from the estimated width of the subject in the at least one location in the at least one image 215. In some cases, a first image 215 of the at least one image 215 of the subject 214 show the front view of the belly area of the subject and the estimated width of the subject is determined. A second image of the at least one image 215 of the same subject may be taken from a side view to show a side profile of the belly area of that subject 214 and the estimated width of the subject 214 is determined from the side profile of the belly area in the second image 215. In some cases, the estimated weight is determined from the estimated height and estimated width in the at least one location based on a look-up table cross-referencing weights with combinations of heights and widths of people. The widths of people in some cases includes the width derived from a front pose of the belly area and the width derived from a side profile of the belly area. Accordingly, the look-up table in some cases cross-references estimated weights with the combination of (i) an estimated height, (ii) an estimated width at a particular location derived from a front pose and (iii) an estimated width at a particular location (in some cases the same location) derived from a profile pose of the subject, or in other cases the look-up table cross-references estimated weights with one or two of the following: (i) an estimated height, (ii) an estimated width at a particular location derived from a front pose of the at least one image 215 and (iii) an estimated width at a particular location (in some cases the same location) derived from a profile pose of the at least one image 215 of the subject 214.

In general, in this patent application, front images 215 and profile images 215 of the at least one image are merely non-limiting examples of the types of poses that may be used for each image in the at least one image 215.

Since estimating height in most embodiments only requires one image and since estimating width in at least some embodiments utilizes two images (for example a view from the front and a profile view), discussions herein of determining height (particularly when height is referred to alone) refer to estimating the height of the subject in "an image" or in "the image" whereas discussions of determining width or both width and height refer to estimating the width of the subject in "at least one image".

In some embodiments, the at least one location of the subject is a front belly area of the subject. In other embodiments, or in other images used in the same embodiment (for example together with front belly area poses), the at least one location of the subject is a profile belly area of the subject. In some cases, the at least one location of the subject is a front belly area of the subject in a first image and a profile belly area of the subject in a second image. Processing unit 250 may therefore be configured to determine an estimated weight of the subject from the estimated height and from the estimated widths of the subject in the first and second images.

Figure 20A:
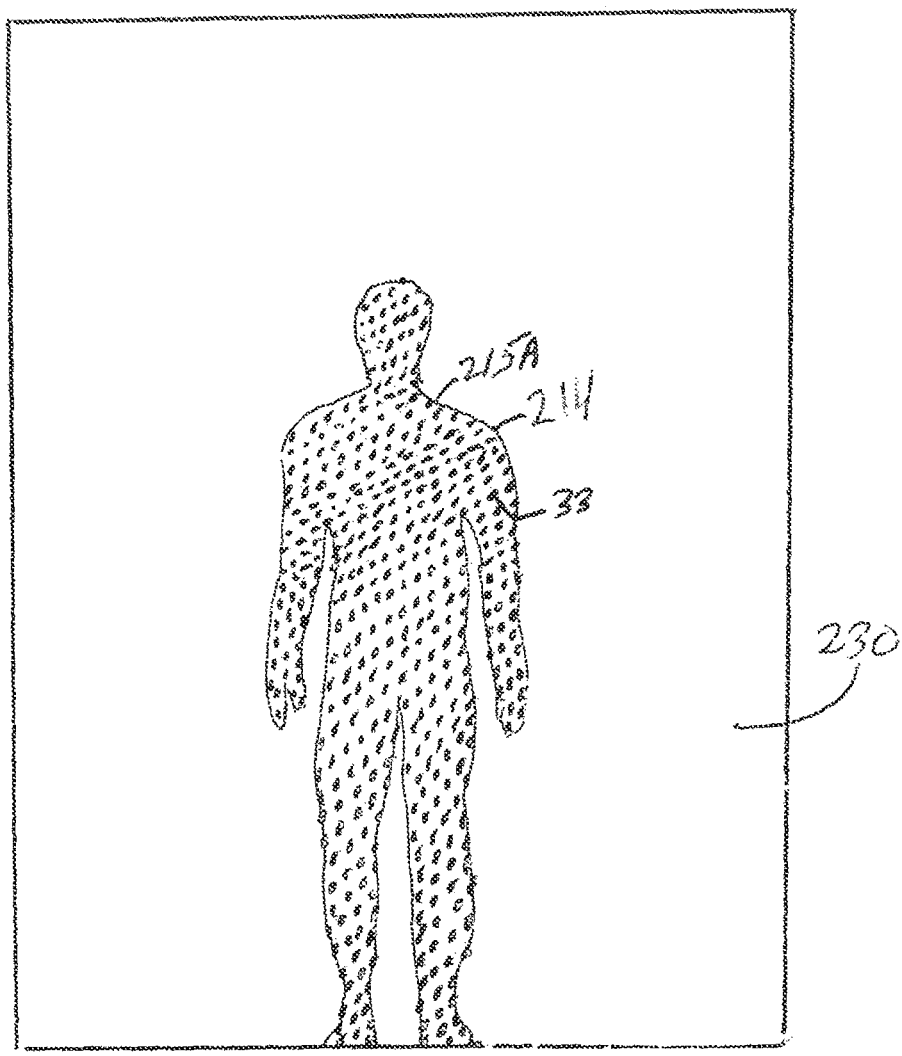
FIG. 20A is a schematic illustration of a front view of a subject shown in a view display of a camera, occupying a certain number of pixels, in accordance with one embodiment of the invention.
Figure 20B:
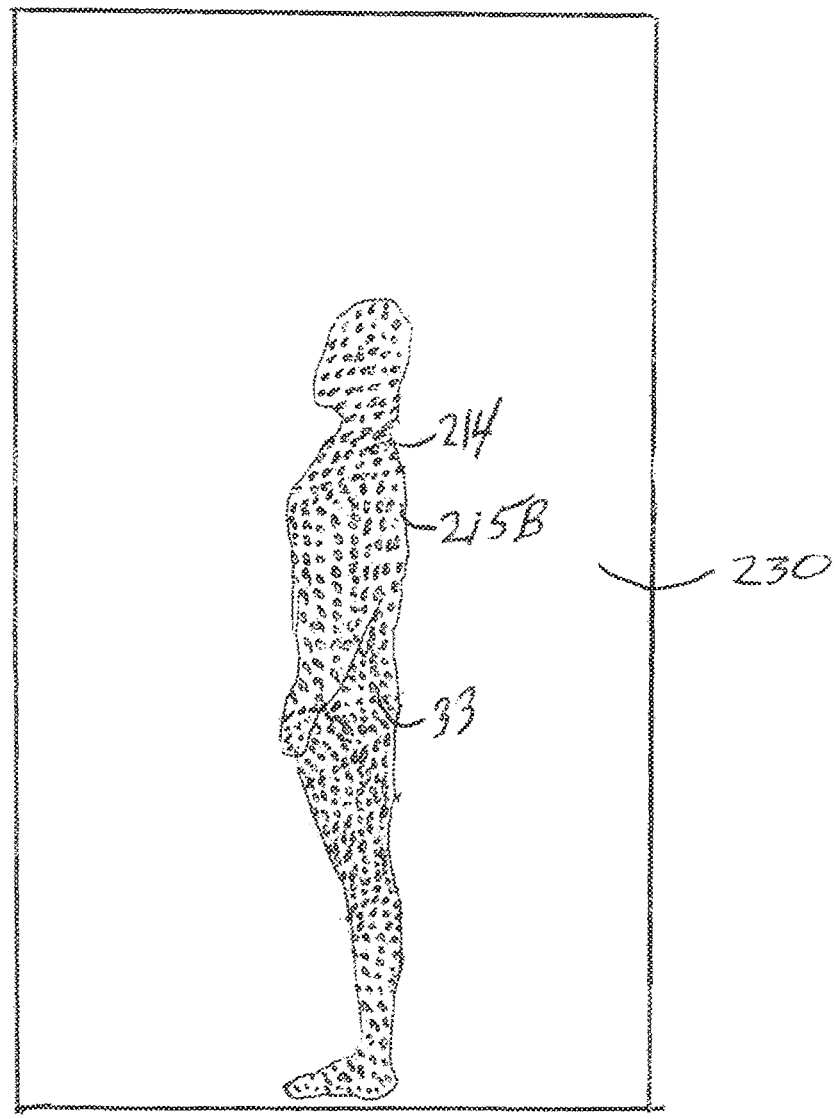
FIG. 20B is a schematic illustration of a profile view of a subject shown in a view display of a camera, occupying a certain number of pixels, in accordance with one embodiment of the invention.

In another embodiment of the invention illustrated in FIG. 20A and FIG. 20B, apparatus 210 is configured to determine an estimate body size parameter of a subject. Apparatus 210 may comprise a digital camera 220 having a view display 230 for displaying the subject 214 entirely within the view display, an application 240 and a processing unit 250 for executing the application 240, the application including program code, and a memory for storing at least one image of a subject viewed in the view display 230.

Processing unit 250 may be configured to determine a number of pixels occupied by the subject in the at least one image 215A, 215B and to determine the estimated body size parameter (i.e. estimated weight, estimated volume, estimated area) of the subject 214 from at least one look-up table correlating the number of pixels 33 occupied by the subject with the estimated body size parameter.

In one example, the at least one image is one image. In another example, the at least one image 215 comprises a front image 215A (FIG. 20A) and a profile image 215B (FIG. 20B) of the same subject 214. Note that although the subjects 214 depicted in FIG. 20A and FIG. 20B appear different, the subjects 214 can just as well be the same subject 214 shown in two different poses.

In this example, the at least one look-up table may comprise a first look-up table correlating the number of pixels occupied in the front image 215A (FIG. 20A) with the estimated body size parameter and a second look-up table correlating the number of pixels occupied in the profile image 215A (FIG. 20B) with the estimated body size parameter, or a single look-up table with multiple axes, includes an axis for each view and an axis for the combination of views of the at least one image. Processing unit 250 may be configured to determine the estimated body size parameter by using one of (i) the front image and first look-up table, (ii) the profile image and second look-up table (iii) both the front image 215A and the profile image 215B and a look-up table that correlates the combination of the two images 215 to whatever estimated body size parameters are derived from the front image and from the profile image.

In one example, the estimated body size parameter is an estimated weight of the subject 214. For example, this can be used for BMI or for just the estimated weight of the subject 214. In another example, the estimated body size parameter is an estimated volume of the subject, or an estimated area of the subject. One example of a use for volume and area body size parameters of a subject is for assisting tailors or others in determining how much material is needed to make an article of clothing for the subject.

Where the body size parameter is an estimated area of the subject 214, the area is along the two dimensions most completely visible when viewing the subject from an image of the at least one image. In the most common case, these two dimensions would be the vertical and horizontal dimensions of the area of the subject in the at least one image seen from a front view of the subject.

Figure 19A:
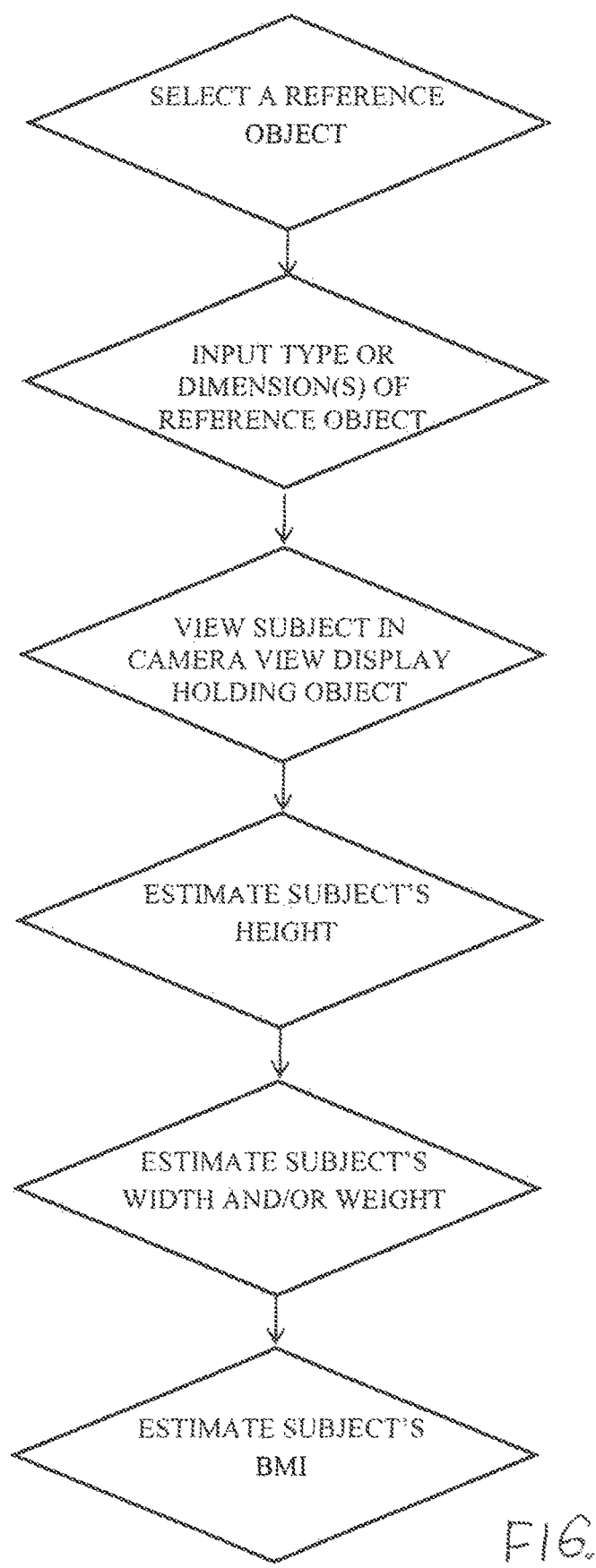
FIG. 19A is a flow chart of a method for determining an estimated height, width, weight and/or BMI of a subject, in accordance with one embodiment of the invention.

In a further embodiment shown in FIG. 16C and FIG. 19, the invention is an apparatus for determining a body mass index (BMI) of a subject. Apparatus 210 may comprise a digital camera 220 having a view display 230 for displaying the subject 214 entirely within the view display 230, an application 240 and a processing unit 250 for executing the application 240, the application including program code, and a memory for storing at least one image 215 of the subject 214 (or another object) viewed in the view display 230 and for storing the vertical and horizontal dimensions of known substantially rectangular reference objects 280.

Figure 19B:
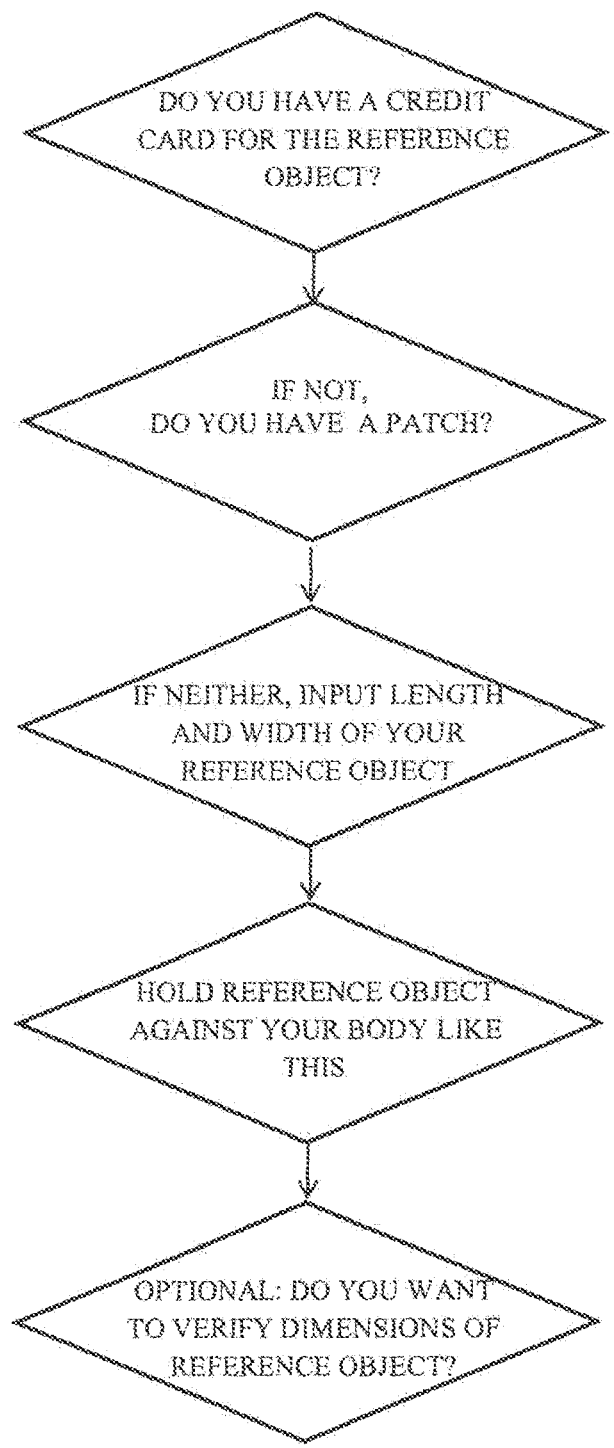
FIG. 19B is a flow chart of user interface prompts used for estimating BMI of a subject, in accordance with one embodiment of the invention.

Application 240 may have a user interface configured to prompt and receive at least one of the following two user inputs: (i) the type of the known substantially rectangular reference object held by the user or (ii) the vertical and horizontal dimensions of a substantially rectangular reference object held by the user. The above discussion and options relating to the details of the user interface is equally applicable to this embodiment for estimating BMI as with regard to the embodiment for estimating the height or width except that the relevant dimensions here are both the horizontal dimension and the vertical dimension. One non-limiting example of a series of prompts by the user interface of application 240 for reference objects used in estimating BMI is illustrated in FIG. 19B.

Processing unit 250 may be configured to determine a magnitude, as measured in pixels 33 in the at least one image, of the vertical dimension of the reference object 280 held by the user, a magnitude of the actual vertical dimension of the reference object 280 held by the user known from one of the two user inputs (namely the type of a known substantially rectangular reference object held by the user or the actual vertical and horizontal dimensions of a substantially rectangular reference object held by the user), a magnitude, as measured in pixels 33 in the at least one image, of the vertical dimension of the subject 214 in the at least one image 215, a ratio of the magnitude, as measured in pixels 33 in the at least one image 215, of the vertical dimension of the reference object 280, and the magnitude of the actual vertical dimension of the reference object 280, and an estimated height of the subject 214 from the magnitude, as measured in pixels 33 in the image, of the vertical dimension of the subject 214 in the at least one image 215, and from the ratio.

Processing unit 250 may further be configured to determine (B) (1) an estimated weight of the subject from a number of pixels 33 occupied by the subject 214 in the image together with a look-up table correlating the number of pixels 33 occupied by the subject with the estimated weight of the subject 214; or alternatively to determine (II) (a) a magnitude, as measured in pixels 33 in the at least one image 215, of the horizontal dimension of the reference object 280 held by the user, (b) a magnitude of the actual horizontal dimension of the reference object held by the user known from one of the two user inputs, (c) a magnitude, as measured in pixels in the at least one image 215, of the horizontal dimension of the subject in the at least one image 215, (d) a ratio of the magnitude, as measured in pixels in the at least one image 215, of the horizontal dimension of the reference object, and the magnitude of the actual horizontal dimension of the reference object, (e) an estimated width of the subject in at least one location of the subject from the magnitude, as measured in pixels in the at least one image 215, of the horizontal dimension of the subject in the at least one image 215, and from the ratio, and (f) the estimated weight from the estimated width and from the estimated height of the subject and from a look-up table correlating estimated weights with combinations of estimated widths and estimated heights.

The discussion and options relating to embodiments for determined an estimated weight of a subject also applies in this BMI embodiment. For example, the estimated width may be derived from more than one image. For example, a first image of at least one image 215 of the subject 214 may show the front view of the at least one location which may be the belly area of the subject and the estimated width of the subject is determined from this view. A second image of at least one image 215 of the same subject may be taken from a side view to show a side profile of the at least one location (i.e. the belly area) of that subject 214 and the estimated width of the subject 214 is determined from the side profile of the belly area in the second image. In some cases, the estimated weight is determined from the estimated height and estimated width in the at least one location based on a look-up table cross-referencing weights with combinations of heights and widths of people. The widths of people in some cases includes the width derived from a front pose of the subject (for example in the belly area) and the width derived from a side profile of the same subject (for example in the belly area). Accordingly, the look-up table in some cases cross-references estimated weights with the combination of (i) an estimated height, (ii) an estimated width at a particular location derived from a front pose and (iii) an estimated width at a particular location (in some cases the same location) derived from a profile pose of the subject.

Furthermore, the discussion and options relating to examples of the at least one location apply mentioned elsewhere in this patent application equally to the BMI embodiment. Further examples of the at least one location (i.e. mid-torso, waist, hips, etc.) are also discussed below with respect to the embodiment for determining estimated width using a contour of the subject.

Processing unit 250 is configured to determine the BMI from the determined estimated height and estimated weight.

In one version of this embodiment, the processing unit 250 is configured to determine the estimated weight of the subject from the number of pixels occupied by the subject in the image and from a the look-up table correlating the number of pixels occupied by the subject with the estimated weight. In one version, apparatus 210 further comprises the substantially rectangular reference object 280, wherein the reference object is one of a credit card and a patch.

Another embodiment of the invention is an apparatus or system, comprising the apparatus 200 described above in any embodiment thereof, together with the substantially rectangular reference object that is held by the user. The reference object is the credit card or the patch or other reference object or any combination of these in certain embodiments.

Figure 18:
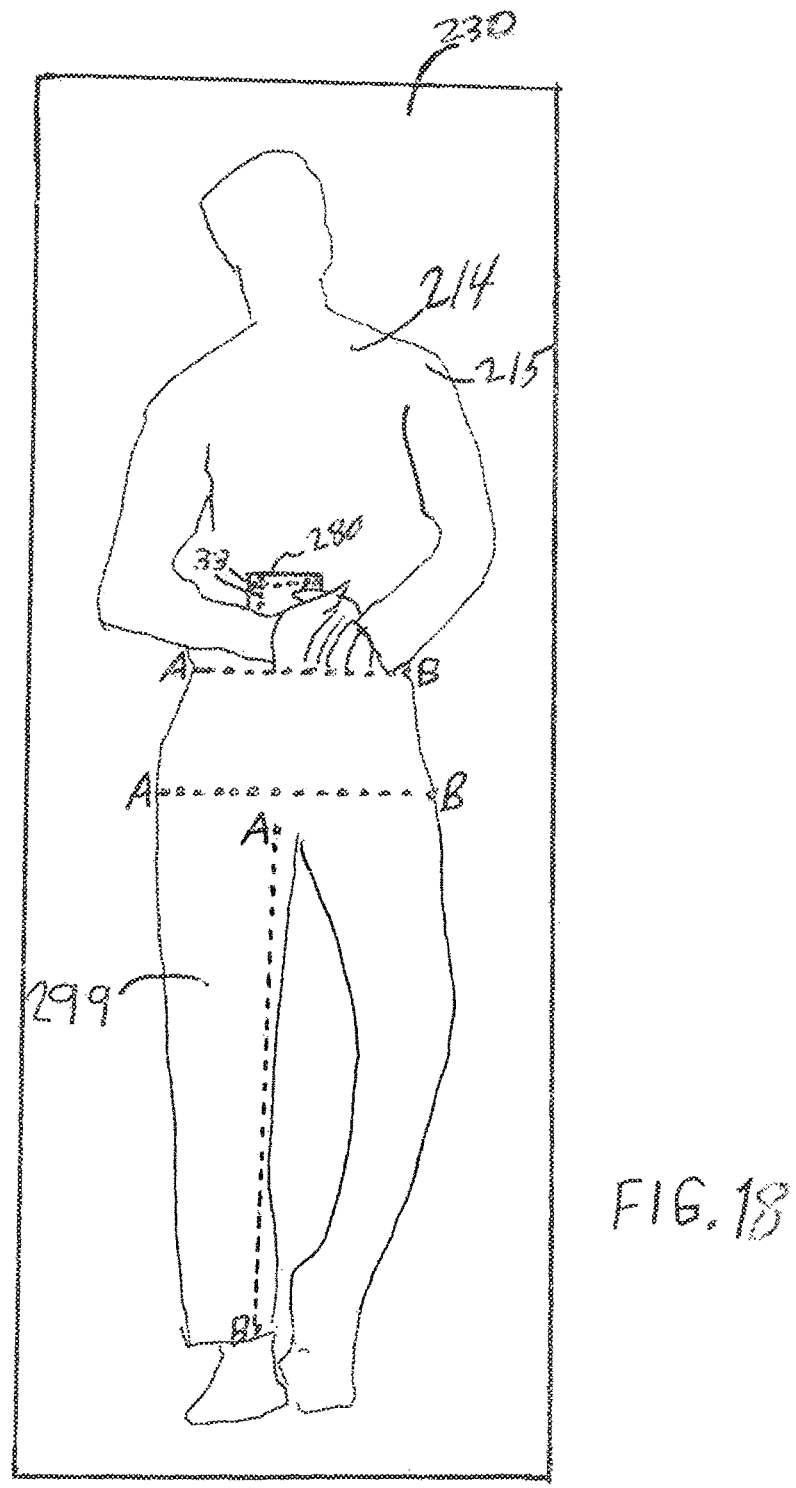
FIG. 18 is a schematic illustration of an object having points A and B worn by a subject shown in a view display of a digital camera, in accordance with one embodiment of the invention.

In an another embodiment of the invention shown in FIG. 18, an apparatus 200 is configured to approximate a distance from point A on a subject 214 or an object 299 to point B on the subject 214 or object 299, such as clothing, held by someone.

Apparatus 200 comprises a digital camera 220 having a view display 230 for displaying an object 299 within the view display 230. Apparatus 200 includes an application 240 having an interface to the camera.

Apparatus 200 also comprises a processing unit 250 for executing the application and including program code and a memory for storing an image of a subject 214, or an object 299 such as clothing, viewed in the view display 230 and for storing a vertical dimension, a horizontal dimension or both vertical and horizontal dimensions of known substantially rectangular reference objects 280, the processing unit 250 configured to determine an estimated distance from point A on the subject 214 or object 299 to Point B on the subject 214 or object 299, by using the application 240. Application may have a user interface configured to prompt and receive at least one of the following two user inputs: (i) the type of the known substantially rectangular reference object 280 held by the user and (ii) the vertical dimension, the horizontal dimension or both the vertical and the horizontal dimensions of a substantially rectangular reference object 280 held by the user.

Processing unit 250 is configured in this embodiment to determine the estimated distance from point A on the subject 214 or object 299 to Point B on the subject 214 or object 299, along a straight line or along a curve, on the object 299 from (i) a magnitude, as measured in pixels 33 in the at least one image 215, of the vertical and/or horizontal dimension of the reference object 280 held by the user, (ii) a magnitude of the actual vertical and/or actual horizontal dimension of the reference object 280 held by the user known from one of the two user inputs, (iii) a magnitude, as measured in pixels in the image, from point A to Point B on the object in the at least one image 215 and a ratio of "(i)" and "(ii)".

In some versions, the object 299 is an article of clothing, for example an article of clothing held by or worn by the subject 214. The object 299 in this embodiment of FIG. 18 is not to be confused with the reference object 280 of the embodiment of FIGS. 16A-17.

In a different embodiment shown in FIG. 1-15, the invention is an apparatus 10 configured to approximate a body mass index (BMI) of a subject 14 using an optical mechanism. Apparatus 10 comprises, in certain embodiments, a digital camera 20 having a view display 30. Typically, apparatus 10 also comprises an application 40 having an interface to the camera 20 as well as a processing unit 50 for executing application 40. Processing unit 50 includes program code and a memory for storing at least one image 15 of the subject 14, the known optical magnification factor of camera 20 and the known distance factor at the time the at least one image 15 of the subject 14 is created.

In any embodiment, when application 40 (or 240) is described herein as configured to perform a certain calculation, it should be understood that application 40 is executed by processing unit 50 (or 250) in order to perform this function. Whenever processing unit (50 or 250) is described as configured to perform something, in some embodiments this is performed using application (40 or 240) and in other embodiments, this is performed using other software or computer instructions or program code. Application 40 (or 240) may optionally be considered part of processing unit 50 (or 250) in some configurations.

The application 40 may either be downloadable in any suitable manner for example from the Internet or an external device or alternatively may be already built into the camera, or may be available through other ways. Camera 20, using application 40, may be configured to display subject 14 being imaged within the view display 30 when a user holds the camera 20 in a direction of the subject 14 such that the view display 30 shows subject 14 as entirely visible within the view display. The view display 30 may include at least a top border 32 known or calculated by the application and a side border 34 known or calculated by the application. The top border 32 and side border 34 may in some embodiments be within a frame (not shown) that is within the view display 30, although this is not absolutely necessary.

In the FIGS. 1-8 and 15, the top border 32 and side border 34 are straight lines, although this is not an absolute requirement in all embodiments.

Application 40 is in some embodiments integrated with a filter 42 configured to determine a contour 44 of an object, for example the subject 14 in the view display, in an image memory. A non-limiting example of such a filter 42 is a contour filter 42. Another non-limiting example of such a filter 42 is an edge-detect filter 42.

Contour 44 comprises in certain embodiments a sequence of points around outer areas of the body of subject 14. In a typical case, as shown in the aforementioned FIGS. 1-9, the contour (which may comprise a sequence of points) envelops the body of subject 14. However, although the subject may be standing with the subject's arms apart from the subject's body, such as in FIGS. 1, 2, 3, 5, 6, 7, 8, 9, the part of the contour 44 that is used by processing unit 50 is the continuous portions of the body of subject 14 and excludes for example the spaces between the arms of the subject 14 and the subject's torso, for example when computing width. In certain embodiments, the sequence of points envelops all portions (or at least all portions) of the body of subject 14 relevant to computing the width or height (or both) of the subject 14 or of the contour 44 of subject 14. For example, the sequence of points in one particular case may include the sides of the body of subject 14 near waist 49 of subject 14. In some embodiments, the sequence of points includes most of the body (or in other embodiments a portion of the body of subject 14 or in other embodiments all but a portion of the body of subject 14) of the subject 14 and that is sufficient to calculate the width of the contour 44 or in other cases the height of the subject 14.

The contour 44 may include a topmost point 45 or a bottommost point 46. The contour 44 may also include left and right side points 47, 48 (i.e. a left side point 47 and a right side point 48) at a waist area 49 of the subject 14.

Apparatus 10 also comprises in some embodiments a distance mechanism 60. Distance mechanism 60 comprises either a user input prompt for the user to input the distance factor (i.e. stating how far the subject 14 is from the camera 20) or a distance factor prompt informing the user how far to place the subject 14 from the camera. In either case, the distance mechanism 60 is for obtaining the distance factor between the camera and the subject 14 to be imaged at the time the at least one image 15 of the subject 14 is created.

Processing unit 50 is in some embodiments configured to determine an estimated height of the subject 14 and an estimated weight of the subject 14 and to determine the body mass index of the subject 14, or an approximated BMI of the subject 14, from the estimated height and estimated weight.

Figure 2:
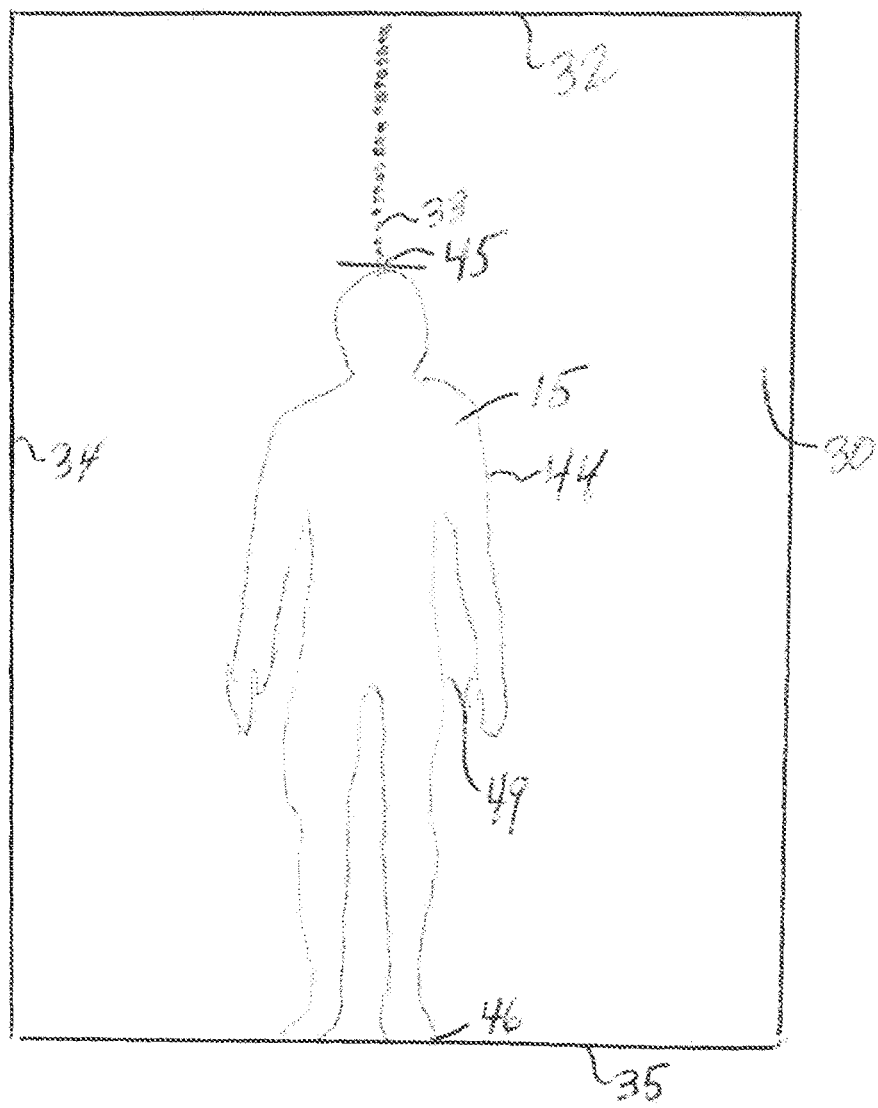
FIG. 2 is a schematic illustration of a subject shown in a digital camera view display, in accordance with one embodiment of the invention.

Processing unit 50 is in some embodiments configured to determine the estimated height of the subject 14 from (i) the known distance factor, (ii) the known optical magnification factor of camera 20 and (iii) a distance, as measured in pixels 33, from the topmost point 45 of the subject 14 to the top border 32 or from the topmost point 45 of the subject 14 to the bottommost point 46 of the subject 14. If as shown in FIG. 2 the subject 14's bottommost point 46, for example, the bottom of his or her feet, is made by the user to coincide with a lower border 35 of the view display 30, then the estimated height may be obtained from the distance, as measured in pixels 33, from the topmost point of the subject 14 to the top border of view display 30 because the distance from the top border to the topmost point of the subject 14 plus the height of the subject 14—in pixels 33—equals the total number of pixels 33 from the top border 32 to the bottom border 35 of the view display 30 (or of the frame). This scenario is shown in FIG. 2.

Figure 8:
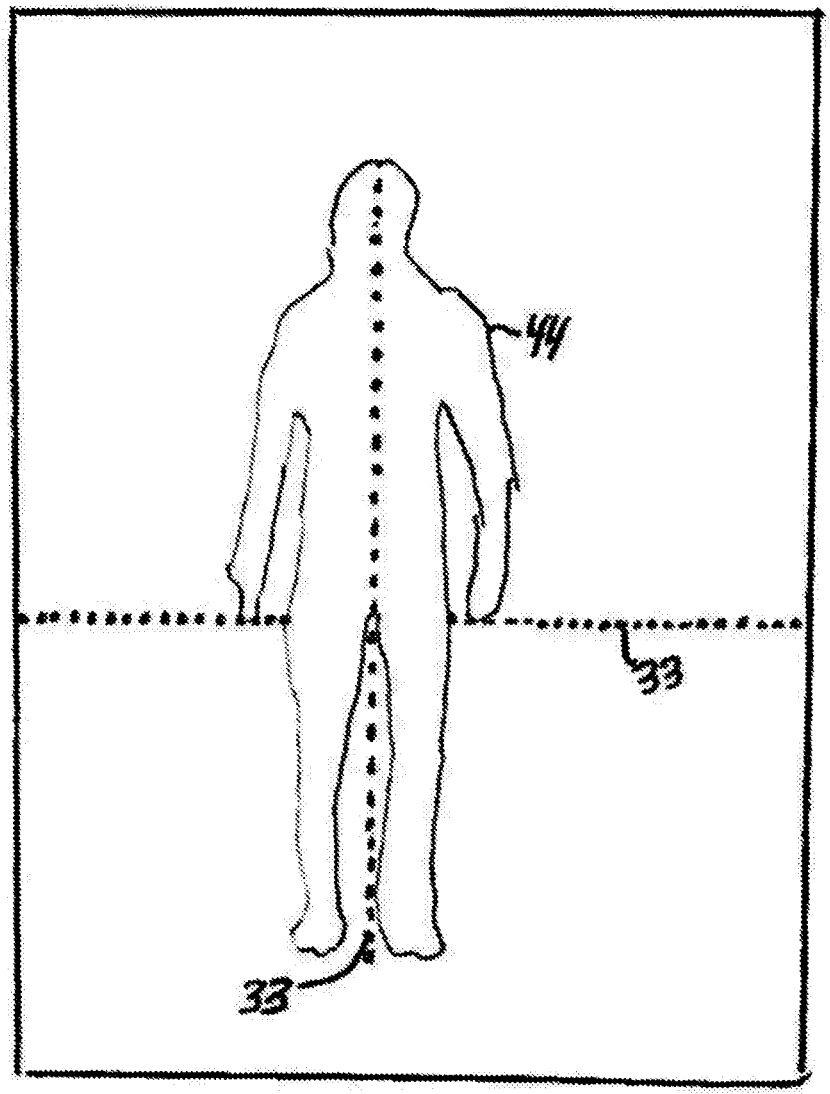
FIG. 8 is a schematic illustration of a subject shown in a digital camera view display, in accordance with one embodiment of the invention.
Figure 9:
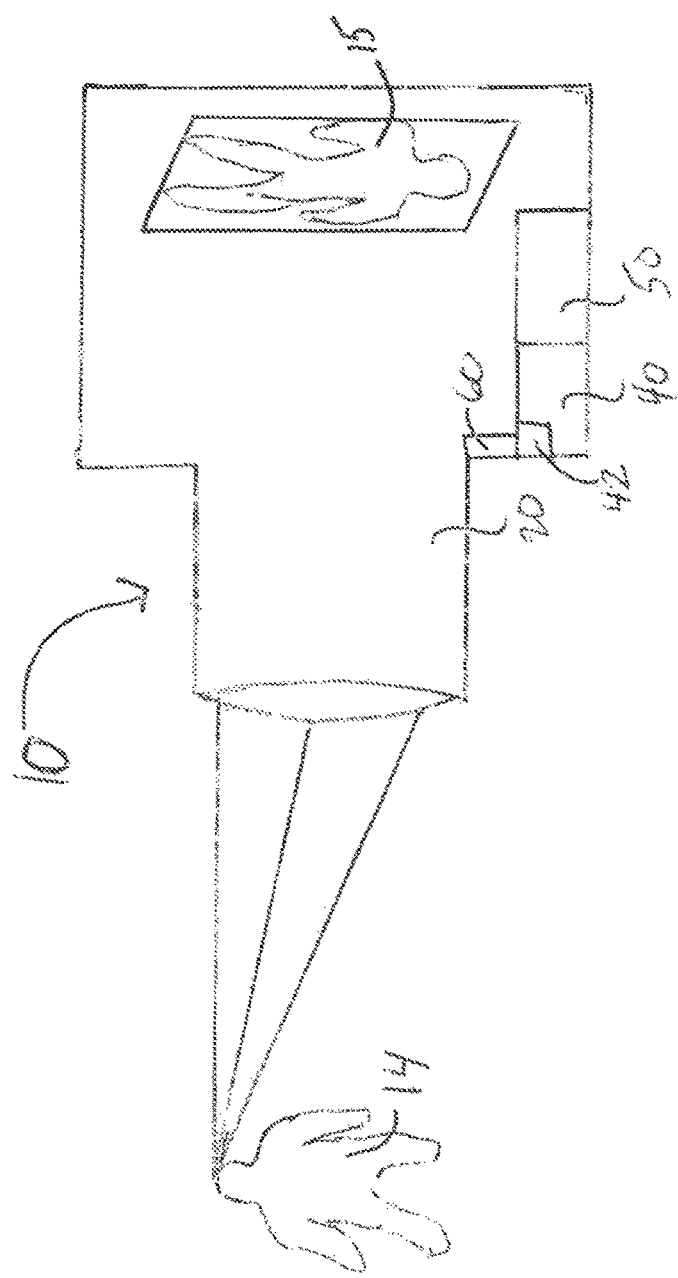
FIG. 9 is a schematic illustration of the operation of a digital camera, in accordance with one embodiment of the invention.
Figure 10:
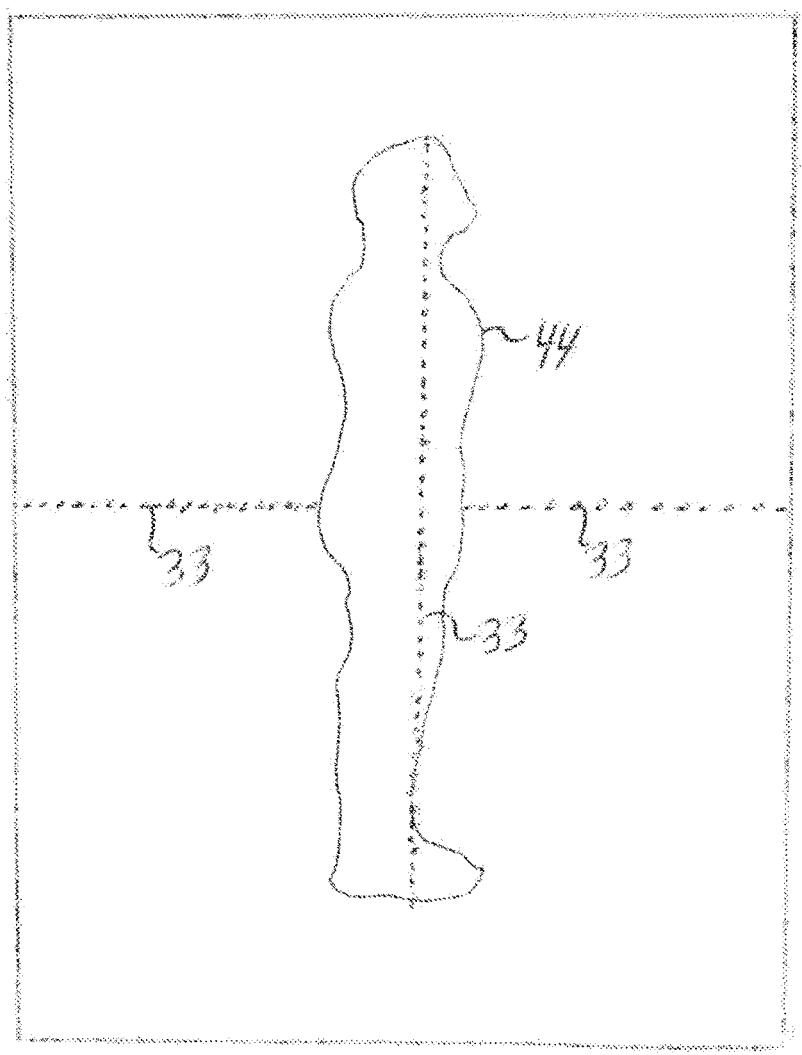
FIG. 10 is a schematic illustration of a side pose of a subject shown in a digital camera view display, in accordance with one embodiment of the invention.
Figure 11:
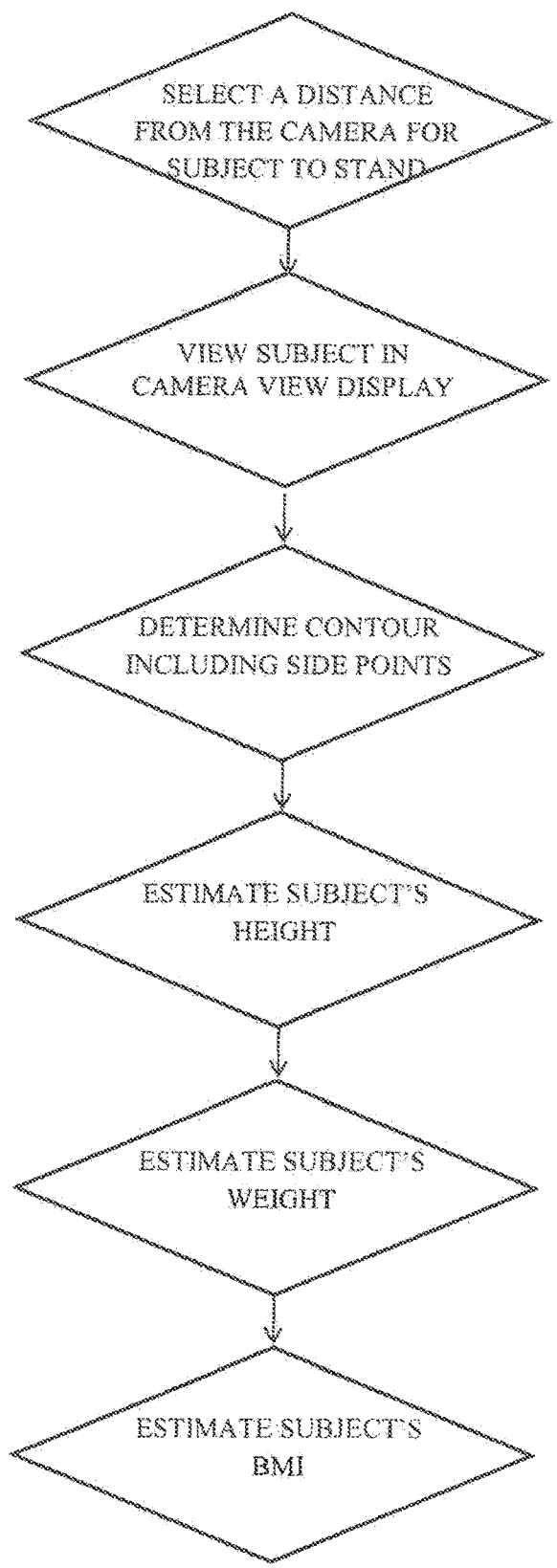
FIG. 11 is a flow chart of a method, in accordance with one embodiment of the invention.
Figure 12:
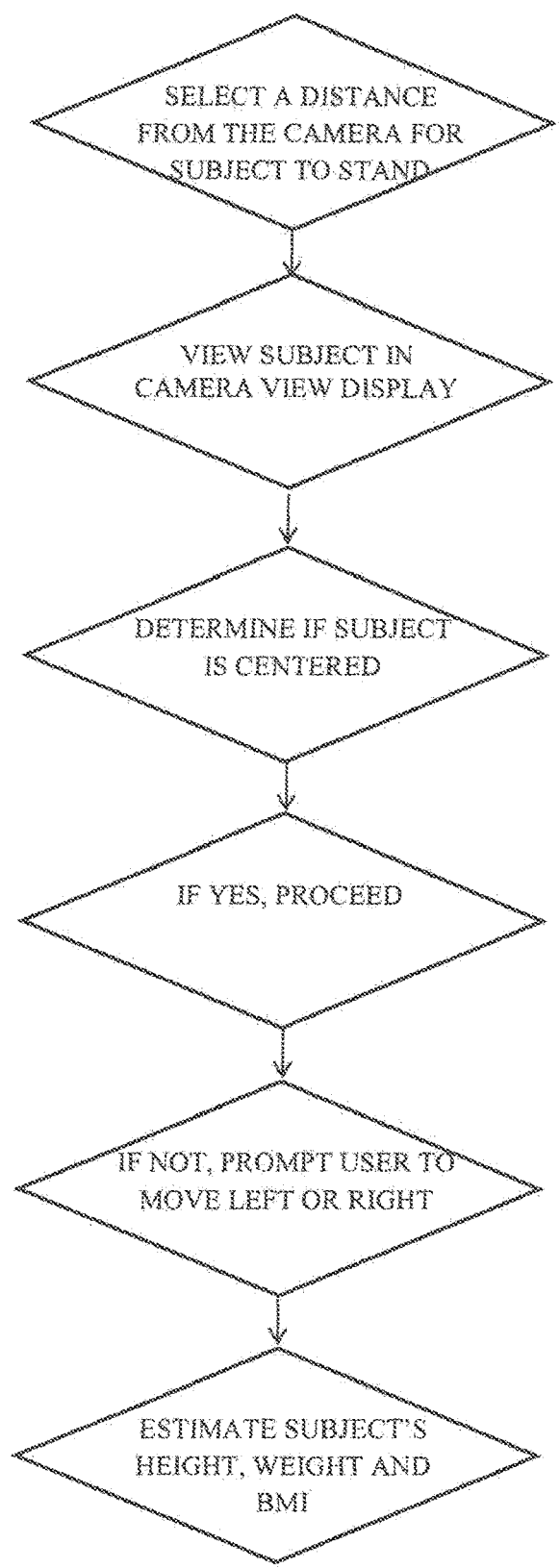
FIG. 12 is a flow chart of a method relating to a centering feature, in accordance with one embodiment of the invention.
Figure 13:
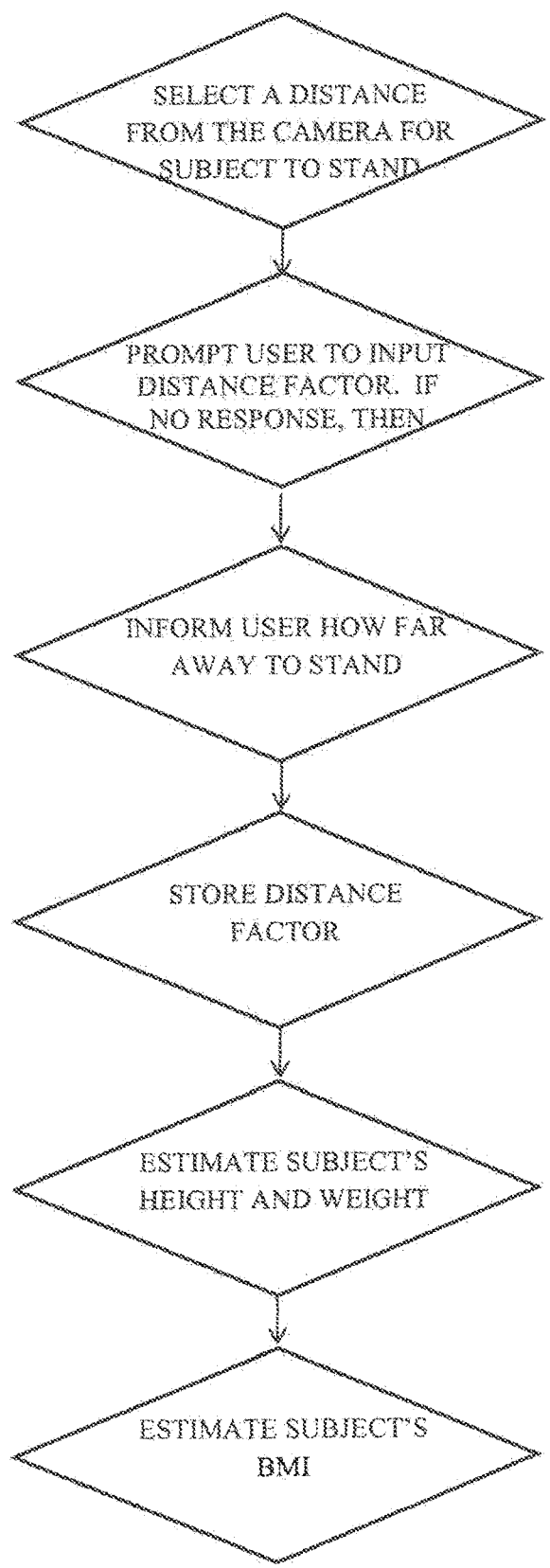
FIG. 13 is a flow chart of a method relating to a distance factor, in accordance with one embodiment of the invention.
Figure 14:
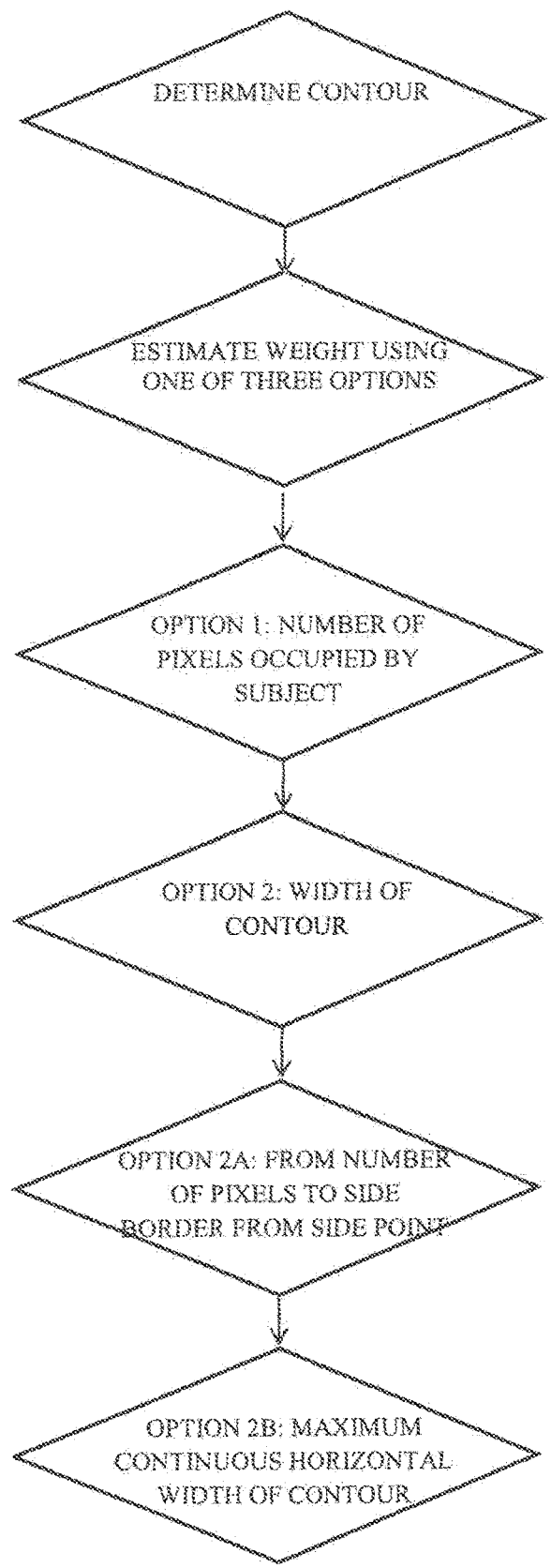
FIG. 14 is a flow chart of a method relating to determining an estimated weight of a subject, in accordance with one embodiment of the invention.

If, however, the subject 14's lowermost point, for example, the bottom of his or her feet, do not coincide with a lower border 35 of the view display 30, then the estimated height of the subject 14 may be obtained from the distance, as measured in pixels 33, from the topmost point of the subject 14 to the bottommost point of the subject 14. This scenario is shown in FIG. 1 and FIG. 8.

Figure 5:
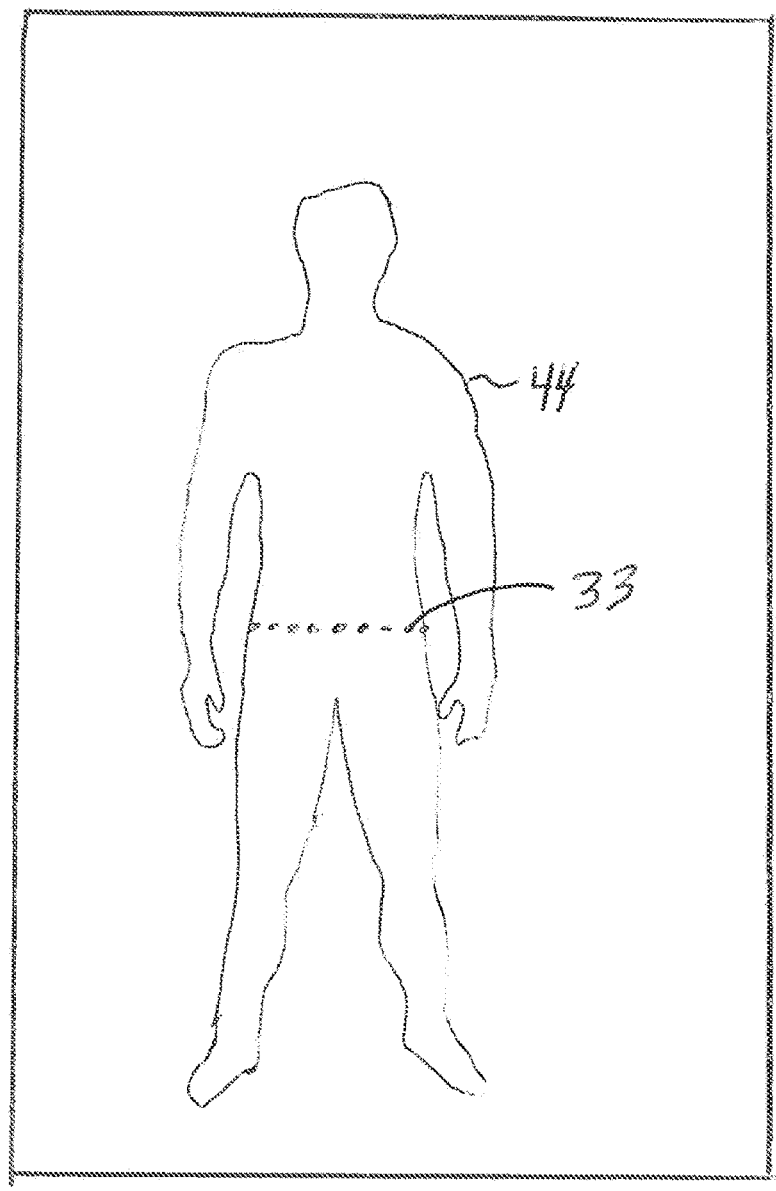
FIG. 5 is a schematic illustration of a subject shown in a digital camera view display, in accordance with one embodiment of the invention.

View display 30 of camera 20 is typically made of distinct pixels 33. In one embodiment, the pixels 33 are ordered vertically and horizontally. The processing unit 50 is in some embodiments configured to count distinct pixels 33 on view display 30 (or at least those necessary to carry out the function of the invention) and to convert a quantity of such pixels 33 of the view display 30 into a distance quantity. Non-limiting examples of the distance quantity include millimeters, centimeters or meters (or inches, feet or yards). The distance quantity may for example be a distance that defines the height of the subject 14 or the width of the subject 14 (whose image 15 has been created after being viewed in the view display 30) or another distance along the body of the subject 14. The width referred to in some embodiments is a continuous horizontal width or a maximum continuous horizontal width of a contour 44 of the subject 14, for example as shown in FIG. 5 (no spaces between body portions included). Typically, the width of contour 44 is determined at a suitable height of the subject 14, for example at a waist area 49 of the subject 14.

Processing unit 50 is in some embodiments also configured to determine an estimated weight of the subject 14 derived from at least one of the following (i) the number of pixels 33 occupied by the subject 14 together with a look-up table converting the number of pixels 33 occupied with the estimated weight, (ii) the estimated height of the subject determined above and an estimated width of the contour 44 of the subject 14 obtained from the left and right side points and from a number of pixels 33 from the left side point to a left side border and a number of pixels 33 from the right side point to a right side border, or the estimated width of the contour 44 of the subject 14 obtained from a number of pixels 33 in the maximum continuous horizontal width of the contour 44, for example together with a look-up table correlating estimated weights with combinations of estimated heights and contour widths (or maximum continuous horizontal widths).

Figure 7A:
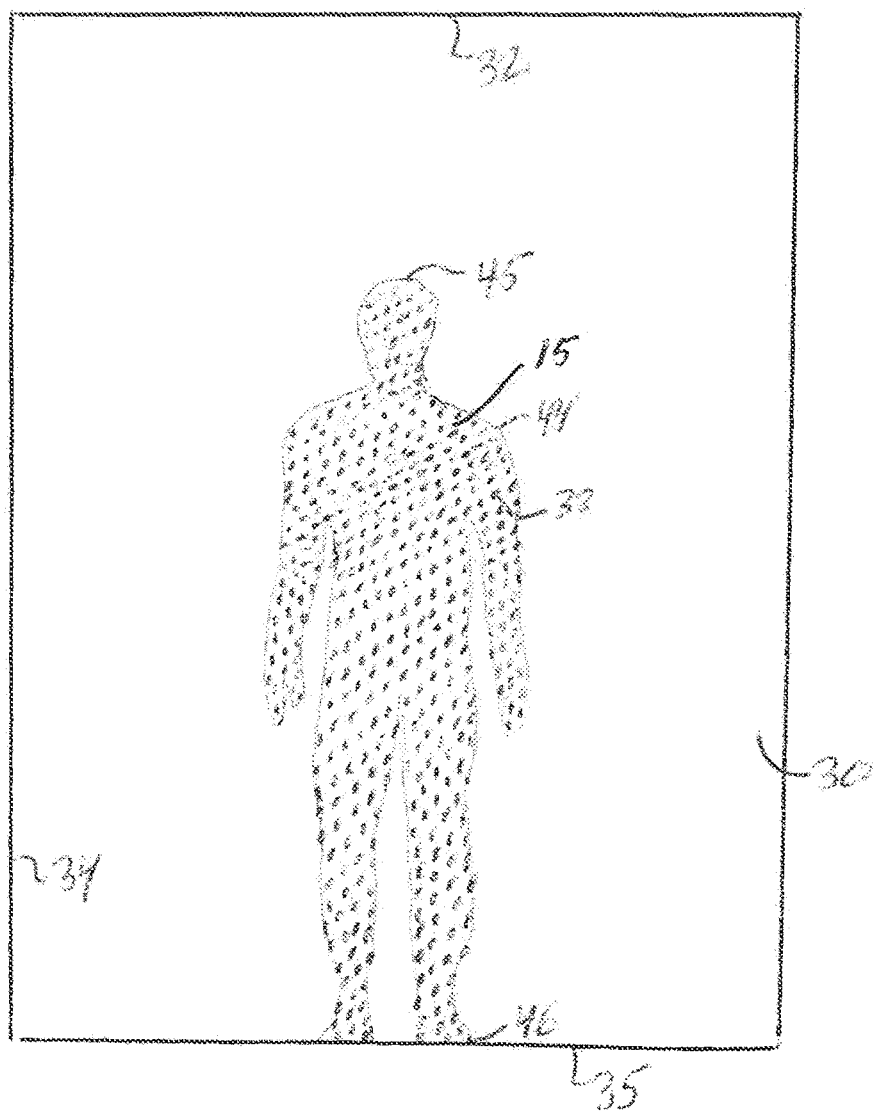
FIG. 7A is a schematic illustration of a front view of a subject shown in a digital camera view display, in accordance with one embodiment of the invention.

As shown in FIG. 7A and FIG. B, the number of pixels 33 occupied by the subject 14 is determined from the contour 44 obtained by filter 42 and the ability of the processing unit 50 to count pixels 33 in a particular defined area of the view display 30. The look-up table converts the number of pixels 33 occupied by the subject 14 in the view display with the estimated weight of the subject 14. The data in the look-up table may be obtained and stored in the memory of the processing unit 50 of camera. This data may be obtained by learning the actual weight of various subject 14s and determining the number of pixels 33 that they occupy in the image seen in the view display 30. Once learned, the data is stored in camera 20.

In this embodiment, it should be understood that "estimated volume" or "estimated area" may be substituted for "estimated weight". In this embodiment, "estimated weight" of the subject may also be generalized to "estimated body size parameter" of the subject 14. In case "estimated area" is used, the area is along the two dimensions most completely visible when viewing the subject from the image. In the most common case, these two dimensions would be the vertical and horizontal dimensions of the area of the subject in the at least one image seen from a front view of the subject.

Figure 7B:
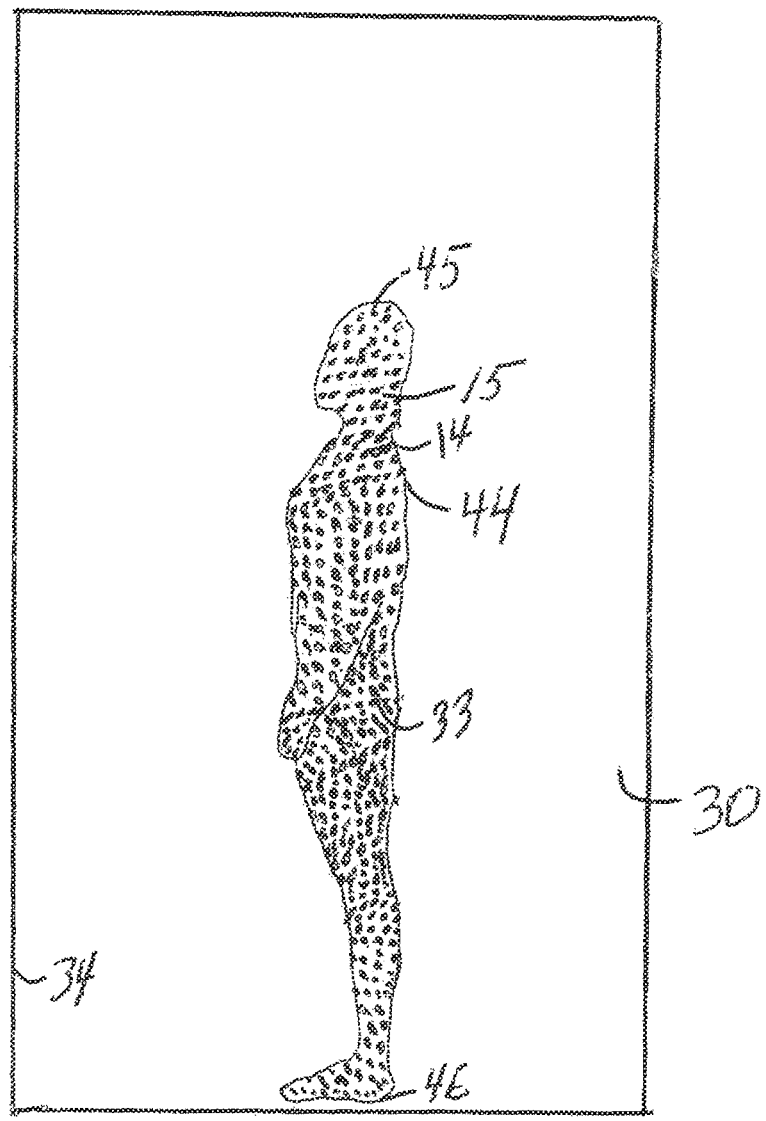
FIG. 7B is a schematic illustration of a profile view of a subject shown in a digital camera view display, in accordance with one embodiment of the invention.

In one non-limiting example of the at least one image, there is one front image (FIG. 7A) and one profile image (FIG. 7B). The processing unit 50 is configured to determine the estimated weight or other body size parameter of the subject 14 after accessing a look-up table stored in the processing unit 50 that correlates estimated weights of various subjects with estimated heights based on the front image, the profile image or both, estimated contour widths based on the front image, the profile image or both or combinations of the estimated heights and estimated widths based on the front image, the profile image or both.

Figure 6:
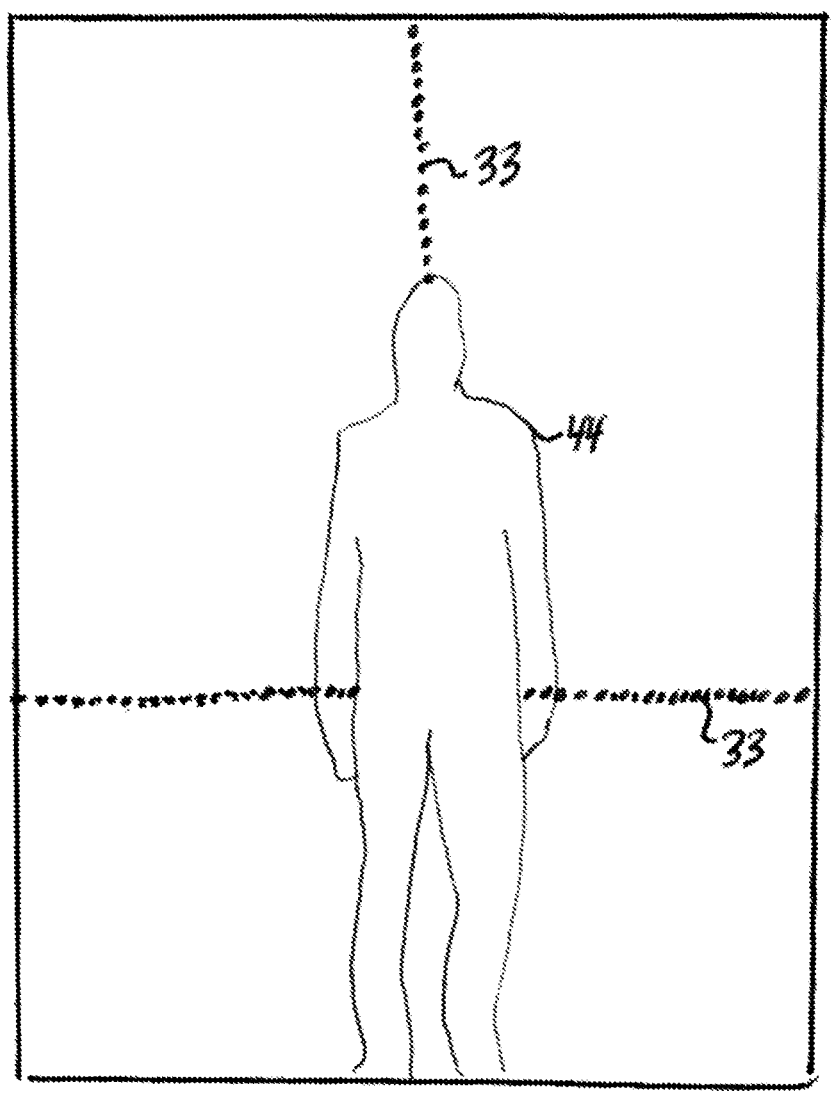
FIG. 6 is a schematic illustration of a subject shown in a digital camera view display, in accordance with one embodiment of the invention.

Processing unit 50 is in some embodiments configured to determine the estimated weight of the subject 14 from a width of the contour 44 of the subject 14. The width of the contour 44 of the subject 14 is obtained in some embodiments from the left and right side points and from a number of pixels 33 from the left side point to a left side border and a number of pixels 33 from the right side point to a right side border. The width of the contour 44 of the subject 14 is obtained in some embodiments from a number of pixels 33 in the maximum continuous horizontal width of the contour 44. As shown in FIG. 5 or FIG. 6, the maximum continuous horizontal width of the contour 44 means that only continuous widths count. This excludes a calculation of width of the contour 44 of the subject 14's body across an area that includes spaces, for example spaces between the legs or spaces between an arm and the waist.

In some embodiments, the weight of subject 14 is estimated using more than one method stated herein or using more than one image of the subject 14 in order to make the estimate more reliable. For example, the weight determined from the number of pixels 33 occupied may be compared to the weight estimated by the width of the contour 44.

The above embodiment is applicable whether the subject 14 poses in a front view or a side view. As shown in FIGS. 1-10, the invention applies to situations in which the subject 14 poses in a front view. The invention also applies, as seen FIG. 10, to situations in which the subject 14 poses in a side view. In any embodiment, there can be both one image of at least one image in the front view and one image of at least one image in a side view.

Processing unit 50 is configured to determine the BMI from the determined estimated height and estimated weight.

In some embodiments, the application 40 is configured to calculate the number of pixels 33 occupied by the subject 14 and the application 40 or processing unit 50 is configured to determine the estimate weight from the number of pixels 33 occupied by the subject 14 and from the look-up table correlating the number of pixels occupied with the estimated weight of the subject.

In certain embodiments, the application 40 is configured to calculate a number of pixels 33 from the left or right side point to the side border 34 and the processing unit 50 is configured to determine the estimated weight from the width of the contour 44 of subject 14. In some cases, processing unit 50 is configured to determine the width of the contour 44 of the subject 14 from the left and right side points and from the number of pixels 33 from the left and right side points to the side border. In other cases, for example as shown in FIG. 5, the application 40 is configured to calculate the number of pixels 33 in the maximum continuous horizontal width of the contour 44 and the processing unit is configured to determine the estimated weight of the subject from the width of the contour of the subject and to determine the width of the contour of the subject 14 from the number of pixels 33 in the maximum continuous horizontal width of the contour 44.

In a further embodiment of apparatus 10 most applicable to a situation in which the subject 14 poses in a front view, processing unit 50 is configured to determine the estimated weight of the subject 14 from at least one of (i) the number of pixels 33 occupied by the subject 14 together with a look-up table converting the number of pixels 33 occupied by the subject with estimated weights, and (ii) a width of the contour 44 of the subject 14, as before. However, in this embodiment the width of the contour 44 of the subject 14 may be obtained (I) from one or both of the left and right side points and from a number of pixels 33 from the one or both of the left and right side points to the side border, or (II) from a number of pixels 33 in the maximum continuous horizontal width of the contour 44. Contour 44 may comprise a sequence of points on outer areas of the body of subject 14.

In one version of this further embodiment, apparatus 10 include a centering feature. For example, the processing unit 50 is configured in some embodiments to determine the estimated weight from the width of the contour 44 of the subject 14 obtained from one of the left 47 and right side points 48 and from a number of pixels 33 from the one of the left and right side points to the side border, and in order to centralize the subject 14 within the view display the processing unit 50 is also configured to determine a number of pixels 33 on the left side of the subject 14 and a number of pixels 33 on the right side of the subject 14 and the camera 20 is configured with a centering prompt.

The processing unit 50 in certain embodiments compares the number of pixels 33 on the left side of the subject 14 to the number of pixels 33 on the right side of the subject 14. The centering prompt is configured in some embodiments to prompt the user to move a certain number of centimeters (or another distance unit) to the left side if the processing unit 50 determines that the number of pixels 33 on the left side of the subject 14 differs from (i.e. is more than) the number of pixels 33 on the right side of the subject 14. Conversely, the centering prompt may be configured to prompt the user to move a certain number of centimeters (or another distance unit) to the right side if the processing unit 50 determines that the number of pixels 33 on the left side of the subject 14 differs from (i.e. is more than) the number of pixels 33 on the right side of the subject 14. The number of centimeters (or another distance unit) that the subject 14 is prompted to move by the centering prompt is based on the conversion of pixels 33 to centimeters and based on the difference in number of pixels 33 between the left 47 and right sides 48 of the subject 14 divided by two. This number of pixels 33 is then converted to centimeters (or another distance) and the subject 14 is prompt to move that distance to whichever direction applies in order to be centered in the view display.

Figure 3:
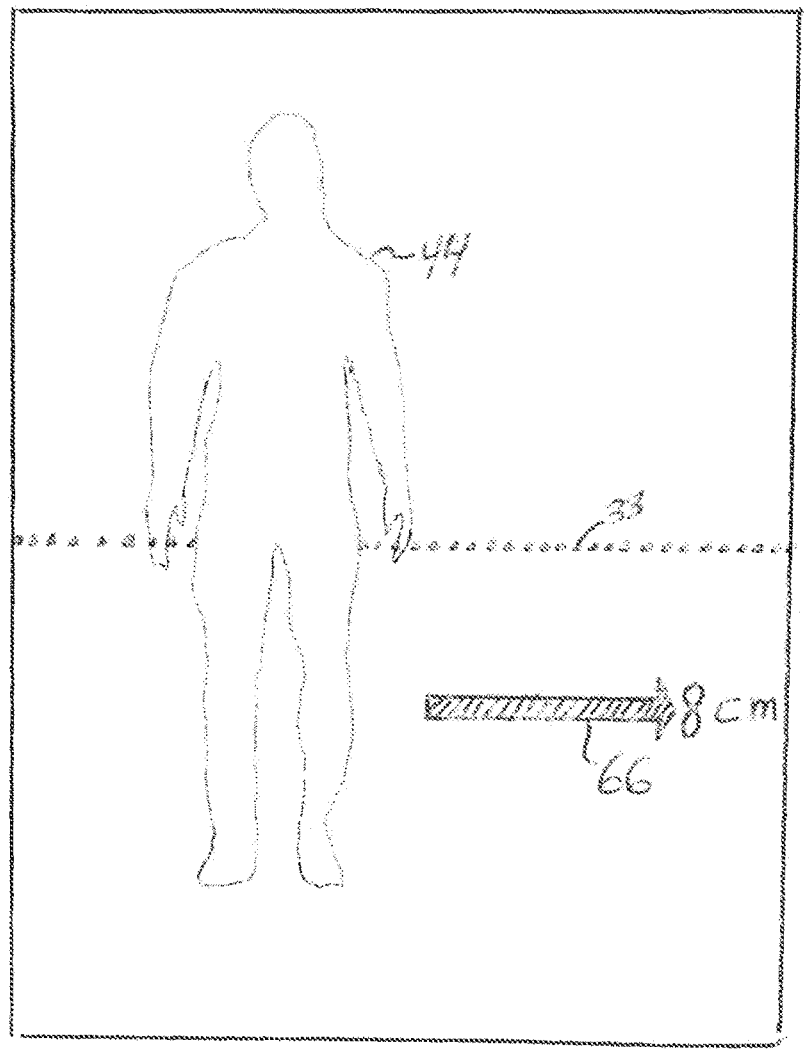
FIG. 3 is a schematic illustration of a subject shown in a digital camera view display, in accordance with one embodiment of the invention.
Figure 4:
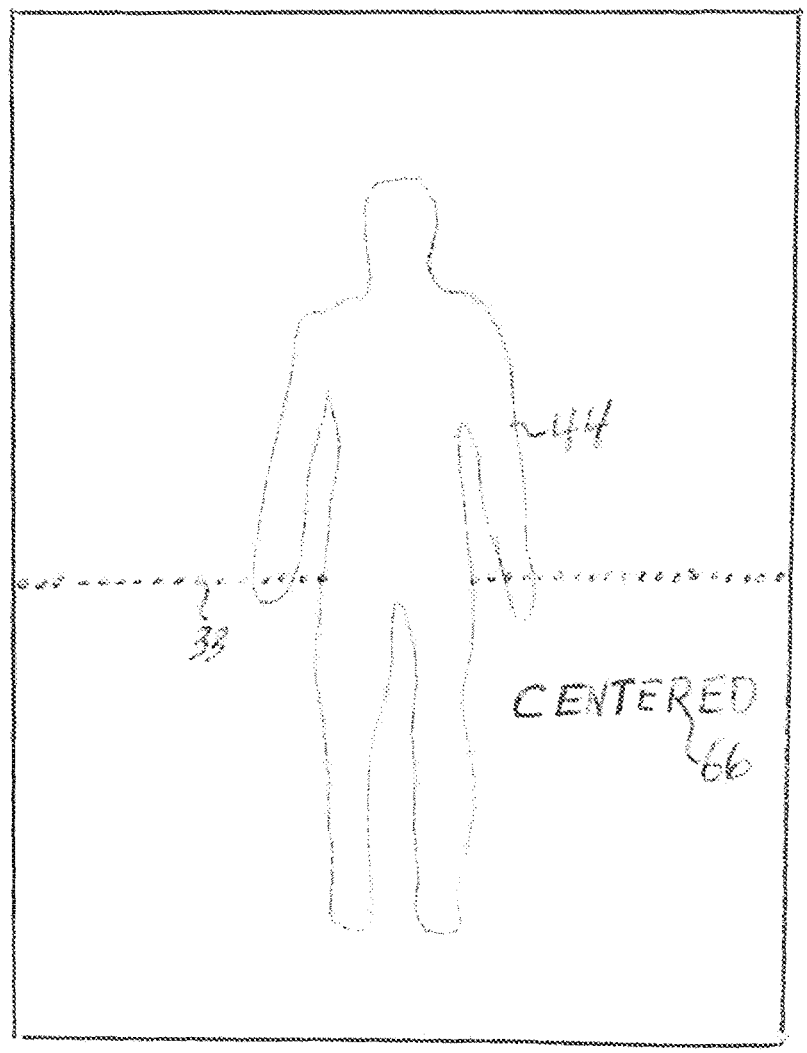
FIG. 4 is a schematic illustration of a subject shown in a digital camera view display, in accordance with one embodiment of the invention.

The centering prompt 66 may be a visual cue that appears on the view display, as shown in FIG. 3, and may include in the visual cue the distance that the subject 14 is suggested to move and direction, as noted by the arrow. Alternatively, the centering prompt 66 may be an audio prompt, or both a visual and audio prompt or some other cue. As shown in FIG. 4, the centering prompt 66 may include a prompt—whether a visual or audio cue or both or another type of cue—confirming that the subject 14 is centered.

In some embodiments, one integrated workflow is used for both the centering prompt and for the distance factor prompt.

Operation of the apparatus 10, in various embodiments, is shown in a collection of flow charts in FIG. 11, FIG. 12, FIG. 13 and FIG. 14. One embodiment of the invention is a method 100 of estimating BMI. This method 100, as other methods of the invention, utilizes components of apparatus 10. The method shown in FIG. 11 includes steps shown in FIG. 11. In one version of a distance mechanism, a user input prompt prompts the user to input the distance factor identify how far the subject 14 is from the camera 20. This can occur even before the user views the subject 14 in the view display 30. In another version, a distance factor prompt of camera 20 informs the user how far to place the subject 14 from the camera at the time the at least one image 15 of the subject 14 is created. In this scenario, this occurs after the user views the subject 14 in the view display 30, or at least after the camera 20 is pointed at the subject 14. In this scenario, the processing unit 50 computes the appropriate distance based on the known magnification factor and the size of the subject 14 and the size of the view display 30.

In another step, the filter 42 of application 40 determines a contour 44 of the subject 14.

Figure 15:
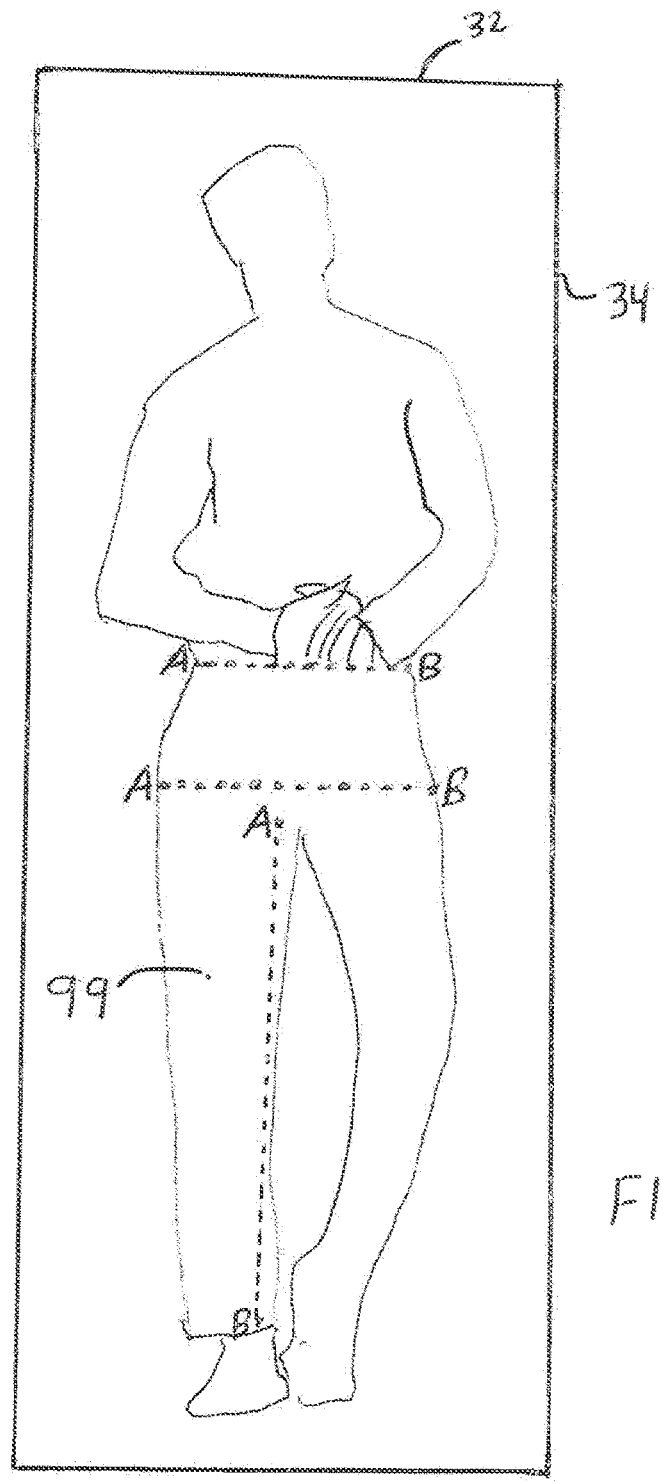
FIG. 15 is a schematic illustration of an object shown in a digital camera view display, in accordance with one embodiment of the invention.

In another embodiment of the invention illustrated in FIG. 15, the invention is an apparatus 10 configured to approximate a distance from point A on a subject 14 or on an object 99 such as an article of clothing 99 to point B on the subject 14 or object 99, using an optical mechanism. Apparatus 10 comprises a digital camera 20 having a view display 30 and an application 40 having an interface to the camera 20, wherein the application 40 is programmed to display the subject 14 or object 99 within the view display 30. In some versions the view display may include a top border 32 known or calculated by the application 40 and a side border 34 known or calculated by the application 40, although the distance from point A on subject 14 or object 99 to point B on subject 14 or object 99 may in some cases be determined by apparatus 10 without reference to top border 32 or side border 34.

Subject 14 or object 99 should be visible entirely within the view display 30. Camera 20 has a known optical magnification factor.

Apparatus 10 may also include, as in other embodiments, a distance mechanism 60 that may comprise either a user input prompt for the user to input the distance factor or a distance factor prompt informing the user how far to place the subject 14 or object 99 from the camera 20, the distance mechanism 60 for obtaining the distance factor between the camera 20 and the subject 14 or object 99 to be imaged at a time an image of the object 99 is created.

Apparatus 10 may further include a processing unit 50 for executing the application 40 and including program code and a memory for storing the image, the known optical magnification factor and the known distance factor at the time the image of the subject 14 or object 99 is created.

The processing unit 50 is configured to determine an estimated distance, for example a metric distance in centimeters or a distance in inches or other units of distance, from a point A to a Point B within (i.e. on) the subject 14 or object 99, wherein the estimated distance is derived by converting the total pixels 33 from point A to point B into a distance by using (i) the known distance factor from the camera 20 to the subject 14 or object 99 and (ii) the known optical magnification factor. As in other embodiments, processing unit 50 is configured to count distinct pixels 33 on view display 30 (or at least those necessary to carry out the function of the invention) and to convert a quantity of such pixels 33 of the view display 30 into a distance quantity.

In some embodiments, the object 99 is a body of a human subject. In other embodiments, the object 99 is an article of clothing which may be held by or worn by the human subject 14.

As illustrated in FIG. 15, using a pair of pants as one non-limiting example of an object 99, a user of apparatus 10 may choose to use camera 20 to measure a distance from point A to point B on the object 99. For example, by doing so, the user may measure the waist, hips and/or inseam of a pair of men's pants that he is wearing or holding. If these pants are the pants that the user came into the store wearing, then measuring these pants can avoid the user having to try on the pants he is considering purchasing. Alternatively, the user could measure the pair of pants he is considering purchasing by holding that pair of pants in front of digital camera 20 in order to measure from point A to point B along the pair of pants he is holding (for example, with the assistance of someone holding the camera 20).

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. Apparatus configured to determine an estimated body size parameter of a subject, comprising:
   a digital camera having a view display for displaying the subject entirely within the view display;
   an application;
   a processing unit for executing the application, the application including program code, and a memory for storing at least one image of the subject viewed in the view display,
   the processing unit configured to determine a number of pixels occupied by the subject in the at least one image and to determine the estimated body size parameter of the subject from at least one look-up table correlating the number of pixels occupied by the subject with the estimated body size parameter, wherein the at least one image comprises a front image and a profile image, wherein the at least one look-up table comprises a first look-up table correlating the number of pixels occupied in the front image with the estimated body size parameter and a second look-up table correlating the number of pixels occupied in the profile image with the estimated body size parameter and wherein the estimated body size parameter is determined by the processing unit using at least one of (i) the front image and first look-up table and (ii) the profile image and second look-up table.

2. The apparatus of claim 1, wherein the estimated body size parameter is an estimated weight of the subject.

3. The apparatus of claim 1, wherein the estimated body size parameter is an estimated volume of the subject.

4. The apparatus of claim 1, wherein the body size parameter is an estimated area of the subject, along the two dimensions most completely visible when viewing the subject from an image of the at least one image.

5. Apparatus configured to approximate a body mass index (BMI) of a subject using an optical mechanism, comprising:
   a digital camera having a view display for displaying the subject entirely in the view display;
   an application having an interface to the camera, the view display including a top border known or calculated by the application and a side border known or calculated by the application,
   the application integrated with a filter configured to determine a contour of a subject in an image memory, the contour including a topmost point or bottommost point and including left and right side points at a mid-torso area of the subject, the subject visible entirely within the view display, the camera having a known optical magnification factor,
   a distance mechanism comprising either a user input prompt for the user to input the distance factor or a distance factor prompt informing the user how far to place the subject from the camera, the distance mechanism for obtaining the distance factor between the camera and the subject to be imaged at a time at least one image of the subject is created;

a processing unit for executing the application, the application including program code, and a memory for storing the at least one image, the known optical magnification factor and the known distance factor at the time the at least one image of the subject is created, the processing unit configured to determine (A) an estimated height of the subject derived from (i) the known distance factor, (ii) the known optical magnification factor and (iii) a distance, as measured in pixels, from the topmost point of the subject to the top border or from the topmost point of the subject to the bottommost point of the subject, and (B) an estimated weight of the subject derived from the estimated height and from at least one of the following (i) the number of pixels occupied by the subject together with a look-up table converting the number of pixels occupied with the estimated weight, (ii) a width of the contour of the subject obtained from the left and right side points and from a number of pixels from the left side point to a left side border and a number of pixels from the right side point to a right side border, or the width of the contour of the subject obtained from a number of pixels in a maximum continuous horizontal width of the contour, whether the subject poses in a front view or a side view, the processing unit configured to determine the BMI from the determined estimated height and estimated weight.

6. The apparatus of claim 5, wherein the application is configured to calculate the number of pixels occupied by the subject and wherein the processing unit is configured to determine the estimate weight from the number of pixels occupied by the subject together with the look-up table.

7. The apparatus of claim 5, wherein the application is configured to calculate a number of pixels from the left or right side point to the side border and wherein the processing unit is configured to determine the estimated weight from the width of the contour of the subject.

8. The apparatus of claim 7, wherein the processing unit is configured to determine the width of the contour of the subject from the left and right side points and from the number of pixels from the left and right side points to the side border.

9. The apparatus of claim 7, wherein the application is configured to calculate the number of pixels in the maximum continuous horizontal width of the contour and wherein the processing unit is configured to determine the estimated weight of the subject from the estimated height and the width of the contour of the subject and to determine the width of the contour of the subject from the number of pixels in the maximum continuous horizontal width of the contour.

10. The apparatus of claim 7, wherein the contour comprises a sequence of points at outer portions of the subject.

11. The apparatus of claim 7, wherein the estimated weight is derived from the estimated height and the width of the contour using a look-up table cross-referencing weights and combinations of heights and widths.

* * * * *